United States Patent
Rabiner et al.

(10) Patent No.: US 8,790,359 B2
(45) Date of Patent: *Jul. 29, 2014

(54) MEDICAL SYSTEMS AND RELATED METHODS

(75) Inventors: Robert Rabiner, North Reading, MA (US); Bradley A. Hare, Chelmsford, MA (US)

(73) Assignee: Cybersonics, Inc., Erie, PA (US)

( * ) Notice: Subject to any disclaimer, the term of this patent is extended or adjusted under 35 U.S.C. 154(b) by 1087 days.

This patent is subject to a terminal disclaimer.

(21) Appl. No.: 11/750,829

(22) Filed: May 18, 2007

(65) Prior Publication Data

US 2007/0225619 A1  Sep. 27, 2007

Related U.S. Application Data

(63) Continuation of application No. 10/665,445, filed on Sep. 19, 2003, now abandoned, which is a continuation of application No. 09/776,015, filed on Feb. 2, 2001, now Pat. No. 6,652,547, which is a continuation-in-part of application No. 09/618,352, filed on Jul. 19, 2000, now Pat. No. 6,551,337.

(60) Provisional application No. 60/178,901, filed on Jan. 28, 2000, provisional application No. 60/157,824, filed on Oct. 5, 1999.

(51) Int. Cl.
*A61B 17/22* (2006.01)

(52) U.S. Cl.
USPC .......................................... 606/169; 606/170

(58) Field of Classification Search
CPC ............... A61B 17/22004; A61B 17/22012; A61B 17/2202; A61B 17/320068; A61N 7/022

USPC ........ 606/127, 128, 159, 166–185, 169, 171, 606/180, 2.5; 604/22; 601/2, 3; 73/632, 73/640–642; 433/86, 118, 119; 600/437–439, 449, 459, 462, 463

See application file for complete search history.

(56) References Cited

U.S. PATENT DOCUMENTS

| 168,975 A | 10/1875 | Farmer |
| 323,762 A | 8/1885 | White |
| 404,319 A | 5/1889 | Taylor |
| 414,090 A | 10/1889 | Taylor |
| 1,045,326 A | 11/1912 | Ruflin |
| 1,239,451 A | 9/1917 | Belz |

(Continued)

FOREIGN PATENT DOCUMENTS

| CA | 2251096 | 8/1998 |
| CA | 2320300 | 8/1999 |

(Continued)

OTHER PUBLICATIONS

BBI Newsletter, vol. XIII, No. 3, p. 44, Biomedical Business International, 1524 Brookhollow Drive, Santa Ana, California 92705 (1990).

(Continued)

*Primary Examiner* — Kathleen Holwerda
(74) *Attorney, Agent, or Firm* — Ulmer & Berne LLP

(57) ABSTRACT

A medical system includes a sheath and an acoustic reflective element that is capable of amplifying acoustic energy. Methods of using a medical system are also provided herein.

20 Claims, 10 Drawing Sheets

(56) References Cited

U.S. PATENT DOCUMENTS

| | | | | |
|---|---|---|---|---|
| 1,779,478 A | | 10/1930 | Leech | |
| 1,861,769 A | | 6/1932 | Wappler | |
| 2,199,602 A | | 5/1940 | Wright | |
| 2,242,120 A | | 5/1941 | Gardiner | |
| 2,270,922 A | | 1/1942 | Bechmann et al. | |
| 2,321,358 A | | 6/1943 | Bokovoy | |
| 2,514,080 A | | 7/1950 | Mason | |
| 2,742,076 A | | 4/1956 | Klein | |
| 2,838,695 A | | 6/1958 | Thurston | |
| 2,842,176 A | | 6/1958 | Franck | |
| 2,917,691 A | | 12/1959 | De Prisco et al. | |
| 2,990,616 A | | 4/1961 | Balamuth et al. | 433/119 |
| 3,028,752 A | * | 4/1962 | Bacon | 73/642 |
| 3,056,698 A | | 10/1962 | Kleesattel et al. | |
| 3,089,790 A | | 5/1963 | Balamuth et al. | |
| 3,113,225 A | | 12/1963 | Kleesattel et al. | |
| 3,132,548 A | | 5/1964 | Livermont | |
| 3,133,351 A | | 5/1964 | von Seggern | |
| 3,202,021 A | | 8/1965 | Livermont | |
| 3,241,780 A | | 3/1966 | Kitselman | |
| 3,304,449 A | | 2/1967 | Pohlman et al. | |
| 3,315,663 A | | 4/1967 | Goldfarb | |
| 3,401,446 A | | 9/1968 | Obeda et al. | |
| 3,433,226 A | | 3/1969 | Boyd | 606/159 |
| 3,438,824 A | | 4/1969 | Balamuth | |
| 3,486,361 A | | 12/1969 | Vaneman et al. | |
| 3,524,085 A | | 8/1970 | Shoh | |
| 3,526,219 A | | 9/1970 | Balamuth | 600/565 |
| 3,528,410 A | | 9/1970 | Banko | |
| 3,565,062 A | | 2/1971 | Kuris | 606/169 |
| 3,589,363 A | | 6/1971 | Banko | 604/22 |
| 3,614,484 A | | 10/1971 | Shoh | |
| 3,660,186 A | | 5/1972 | Sager et al. | |
| 3,683,736 A | | 8/1972 | Loose | |
| 3,763,680 A | | 10/1973 | Godfrey et al. | |
| 3,805,787 A | | 4/1974 | Banko | 128/276 |
| 3,809,977 A | | 5/1974 | Balamuth et al. | |
| 3,840,932 A | | 10/1974 | Balamuth et al. | |
| 3,853,130 A | | 12/1974 | Sheridan | |
| 3,861,391 A | | 1/1975 | Antonevich et al. | 606/128 |
| 3,890,977 A | | 6/1975 | Wilson | |
| 3,906,954 A | | 9/1975 | Baehr et al. | |
| 3,939,033 A | | 2/1976 | Grgach et al. | |
| 3,955,662 A | | 5/1976 | Thackston | |
| 3,962,898 A | | 6/1976 | Tillmann | |
| 3,967,621 A | | 7/1976 | Schwarz | |
| 3,980,906 A | | 9/1976 | Kuris et al. | |
| 3,988,782 A | | 11/1976 | Dardik et al. | |
| 3,990,452 A | | 11/1976 | Murry et al. | |
| 3,991,929 A | | 11/1976 | Smith | |
| 4,011,474 A | | 3/1977 | O'Neill | |
| 4,012,174 A | | 3/1977 | Seibel et al. | |
| 4,012,647 A | | 3/1977 | Balamuth et al. | |
| 4,044,174 A | | 8/1977 | Carr | |
| 4,063,557 A | | 12/1977 | Wuchinich et al. | |
| 4,069,541 A | | 1/1978 | Williams et al. | |
| 4,083,996 A | | 4/1978 | Tanaka et al. | |
| 4,136,700 A | | 1/1979 | Broadwin et al. | 606/169 |
| 4,142,412 A | * | 3/1979 | McLeod et al. | 73/861.25 |
| 4,143,130 A | | 3/1979 | Imondi et al. | |
| 4,144,646 A | | 3/1979 | Takemoto et al. | |
| 4,157,396 A | | 6/1979 | Tanaka et al. | |
| 4,164,524 A | | 8/1979 | Ward et al. | |
| 4,169,984 A | | 10/1979 | Parisi | 310/323.16 |
| 4,174,410 A | | 11/1979 | Smith | |
| 4,178,935 A | | 12/1979 | Gekhman et al. | |
| 4,203,429 A | | 5/1980 | Vasilevsky et al. | |
| 4,203,444 A | | 5/1980 | Bonnell et al. | |
| 4,223,676 A | | 9/1980 | Wuchinich et al. | |
| 4,225,803 A | | 9/1980 | Goof | |
| 4,236,510 A | | 12/1980 | Hatter et al. | 601/2 |
| 4,248,232 A | | 2/1981 | Engelbrecht et al. | |
| 4,265,928 A | | 5/1981 | Braun | |
| 4,280,233 A | | 7/1981 | Raab | |
| 4,300,564 A | | 11/1981 | Furihata | |
| 4,311,147 A | | 1/1982 | Hausler | |
| 4,315,181 A | | 2/1982 | Holze, Jr. | |
| 4,316,465 A | | 2/1982 | Dotson, Jr. | |
| 4,326,903 A | | 4/1982 | Summo | |
| 4,334,168 A | | 6/1982 | Besson et al. | |
| 4,335,426 A | | 6/1982 | Maxwell et al. | |
| 4,352,570 A | | 10/1982 | Firth | |
| 4,356,590 A | | 11/1982 | Goldsmith | |
| 4,361,044 A | * | 11/1982 | Kupperman et al. | 73/623 |
| 4,363,992 A | | 12/1982 | Holze, Jr. | |
| 4,368,410 A | | 1/1983 | Hance et al. | |
| 4,385,413 A | | 5/1983 | Goldsmith | |
| 4,393,734 A | | 7/1983 | Thorn et al. | |
| 4,395,392 A | | 7/1983 | Wolgemuth | |
| 4,399,003 A | | 8/1983 | Sarig et al. | |
| 4,414,045 A | | 11/1983 | Wang et al. | |
| 4,425,115 A | | 1/1984 | Wuchinich | |
| 4,428,748 A | | 1/1984 | Peyman et al. | |
| 4,445,509 A | | 5/1984 | Auth | |
| 4,447,455 A | | 5/1984 | Madaus et al. | |
| 4,462,242 A | | 7/1984 | Morgenthaler | |
| 4,467,678 A | | 8/1984 | Lindholm | |
| 4,474,180 A | | 10/1984 | Angulo | 128/328 |
| 4,479,585 A | | 10/1984 | Sandhaus | |
| 4,480,642 A | | 11/1984 | Stoy et al. | |
| 4,483,571 A | | 11/1984 | Mishiro | |
| 4,486,680 A | | 12/1984 | Bonnet et al. | 310/323.19 |
| 4,493,694 A | | 1/1985 | Wuchinich | 604/22 |
| 4,498,025 A | | 2/1985 | Takahashi | |
| 4,504,264 A | | 3/1985 | Kelman | 604/22 |
| 4,516,398 A | | 5/1985 | Wuchinich | |
| 4,523,122 A | | 6/1985 | Tone et al. | |
| 4,526,571 A | | 7/1985 | Wuchinich | 604/22 |
| 4,529,115 A | | 7/1985 | Renshaw et al. | |
| 4,530,138 A | | 7/1985 | Ritter | |
| 4,534,819 A | | 8/1985 | Payet et al. | |
| 4,535,659 A | | 8/1985 | Yang | |
| 4,535,759 A | | 8/1985 | Polk et al. | 128/24 A |
| 4,571,520 A | | 2/1986 | Saito et al. | |
| 4,572,041 A | | 2/1986 | Rissmann | |
| 4,576,177 A | | 3/1986 | Webster, Jr. | |
| 4,583,365 A | | 4/1986 | John | |
| 4,587,958 A | | 5/1986 | Noguchi et al. | |
| 4,589,415 A | | 5/1986 | Haaga | |
| 4,601,705 A | | 7/1986 | McCoy | |
| 4,603,694 A | | 8/1986 | Wheeler | |
| 4,605,454 A | | 8/1986 | Sayovitz et al. | |
| 4,607,185 A | | 8/1986 | Elbert et al. | |
| 4,609,368 A | | 9/1986 | Dotson, Jr. | |
| 4,620,545 A | | 11/1986 | Shene et al. | |
| 4,633,119 A | | 12/1986 | Thompson | |
| 4,634,420 A | | 1/1987 | Spinosa et al. | 604/22 |
| 4,642,509 A | | 2/1987 | Kumada | |
| 4,643,717 A | | 2/1987 | Cook et al. | |
| 4,647,336 A | | 3/1987 | Coenen et al. | |
| 4,647,871 A | | 3/1987 | Turner, Jr. | |
| 4,651,043 A | | 3/1987 | Harris et al. | |
| 4,652,785 A | | 3/1987 | Gabriel et al. | |
| 4,652,786 A | | 3/1987 | Mishiro | |
| 4,655,104 A | | 4/1987 | Blattner | |
| 4,663,556 A | | 5/1987 | Kumada | |
| 4,676,975 A | | 6/1987 | Becton et al. | |
| 4,678,993 A | | 7/1987 | Vinnemann et al. | |
| 4,688,454 A | | 8/1987 | Scull | |
| 4,690,722 A | | 9/1987 | Flood | |
| 4,692,139 A | | 9/1987 | Stiles | |
| 4,696,299 A | | 9/1987 | Shene et al. | |
| 4,702,236 A | | 10/1987 | Tarabichy et al. | |
| 4,704,131 A | | 11/1987 | Noishiki | |
| 4,704,573 A | | 11/1987 | Turner, Jr. | |
| 4,708,127 A | | 11/1987 | Abdelghani | |
| 4,713,132 A | | 12/1987 | Abel et al. | |
| 4,715,078 A | | 12/1987 | Howard et al. | |
| 4,718,907 A | | 1/1988 | Karwoski | |
| 4,730,614 A | | 3/1988 | Lacruche et al. | |
| 4,732,152 A | | 3/1988 | Wallsten et al. | |
| 4,732,156 A | | 3/1988 | Nakamura | |
| 4,735,625 A | | 4/1988 | Davidson | |
| 4,738,666 A | | 4/1988 | Fuqua | |

(56) References Cited

U.S. PATENT DOCUMENTS

| | | |
|---|---|---|
| 4,738,667 A | 4/1988 | Galloway |
| 4,747,820 A | 5/1988 | Hornlein et al. |
| 4,748,985 A | 6/1988 | Nagasaki |
| 4,748,986 A | 6/1988 | Morrison et al. |
| 4,749,437 A | 6/1988 | Welter |
| 4,750,488 A | 6/1988 | Wuchinich et al. |
| 4,750,902 A | 6/1988 | Wuchinich et al. |
| 4,751,916 A | 6/1988 | Bory |
| 4,756,304 A | 7/1988 | Watanabe |
| 4,756,309 A | 7/1988 | Sachse et al. |
| 4,758,222 A | 7/1988 | McCoy |
| 4,758,293 A | 7/1988 | Samida |
| 4,762,668 A | 8/1988 | Loose et al. |
| 4,770,730 A | 9/1988 | Abe |
| 4,771,202 A | 9/1988 | Takahashi |
| 4,771,782 A | 9/1988 | Millar |
| 4,791,915 A | 12/1988 | Barsotti et al. |
| 4,794,912 A | 1/1989 | Lia |
| 4,823,723 A | 4/1989 | Brooks |
| 4,823,783 A | 4/1989 | Willhite, Jr. et al. |
| 4,825,851 A | 5/1989 | Cocks et al. |
| 4,828,052 A | 5/1989 | Duran et al. |
| 4,830,002 A | 5/1989 | Semm |
| 4,834,102 A | 5/1989 | Schwarzchild et al. |
| 4,838,853 A | 6/1989 | Parisi ................ 604/22 |
| 4,838,859 A | 6/1989 | Strassmann |
| 4,844,081 A | 7/1989 | Northeved et al. |
| 4,846,161 A | 7/1989 | Roger |
| 4,846,174 A | 7/1989 | Willard et al. |
| 4,846,790 A | 7/1989 | Hornlein et al. |
| 4,850,358 A | 7/1989 | Millar |
| 4,862,573 A | 9/1989 | Kelson et al. |
| 4,866,491 A | 9/1989 | Solomon et al. |
| 4,867,141 A | 9/1989 | Nakada et al. ................ 601/4 |
| 4,870,953 A * | 10/1989 | DonMicheal et al. ........ 606/128 |
| 4,872,333 A | 10/1989 | Burnand |
| 4,873,969 A | 10/1989 | Huebsch |
| 4,877,037 A | 10/1989 | Ko et al. |
| 4,880,011 A | 11/1989 | Imade et al. |
| 4,881,761 A | 11/1989 | Hornlein et al. |
| 4,882,777 A | 11/1989 | Narula |
| 4,885,499 A | 12/1989 | Ueha et al. |
| 4,886,060 A | 12/1989 | Wiksell ................ 128/303.14 |
| 4,886,491 A | 12/1989 | Parisi et al. ................ 304/22 |
| 4,892,089 A | 1/1990 | Cocks et al. |
| 4,904,391 A | 2/1990 | Freeman |
| 4,907,572 A | 3/1990 | Borodulin et al. |
| 4,909,789 A | 3/1990 | Taguchi et al. |
| 4,917,104 A | 4/1990 | Rebell |
| 4,920,954 A | 5/1990 | Alliger et al. ................ 128/24 A |
| 4,922,902 A | 5/1990 | Wuchinich et al. ................ 604/22 |
| 4,924,863 A | 5/1990 | Sterzer |
| 4,931,047 A | 6/1990 | Broadwin et al. ................ 604/22 |
| 4,931,049 A | 6/1990 | Klimas |
| 4,936,281 A | 6/1990 | Stasz |
| 4,960,410 A | 10/1990 | Pinchuk |
| 4,961,424 A | 10/1990 | Kubota et al. ................ 128/24 A |
| 4,962,755 A | 10/1990 | King et al. ................ 601/2 |
| 4,963,151 A | 10/1990 | Ducheyne et al. |
| 4,966,131 A | 10/1990 | Houghton et al. |
| 4,966,148 A | 10/1990 | Millar |
| 4,974,581 A | 12/1990 | Wiksell |
| 4,978,333 A | 12/1990 | Broadwin et al. |
| 4,979,952 A | 12/1990 | Kubota et al. |
| 4,986,808 A | 1/1991 | Broadwin et al. |
| 4,989,583 A | 2/1991 | Hood ................ 128/24 A |
| 4,989,588 A | 2/1991 | Kubota et al. |
| 5,003,965 A | 4/1991 | Talish et al. |
| 5,003,990 A | 4/1991 | Osypka |
| 5,015,221 A | 5/1991 | Smith |
| 5,015,227 A | 5/1991 | Broadwin et al. ................ 604/22 |
| 5,017,379 A | 5/1991 | Lemelson |
| 5,019,083 A | 5/1991 | Klapper et al. |
| 5,024,234 A | 6/1991 | Leary et al. |
| 5,026,387 A | 6/1991 | Thomas ................ 606/169 |
| 5,027,792 A | 7/1991 | Meyer |
| 5,040,548 A | 8/1991 | Yock |
| 5,045,054 A | 9/1991 | Hood et al. |
| 5,046,497 A | 9/1991 | Millar |
| 5,049,157 A | 9/1991 | Mittelmeier et al. |
| 5,054,492 A | 10/1991 | Scribner et al. |
| 5,055,101 A | 10/1991 | McCoy |
| 5,057,106 A | 10/1991 | Kasevich et al. |
| 5,057,119 A | 10/1991 | Clark et al. ................ 606/169 |
| 5,057,182 A | 10/1991 | Wuchinich ................ 156/580.1 |
| 5,058,570 A | 10/1991 | Idemoto et al. |
| 5,059,210 A | 10/1991 | Clark et al. ................ 606/169 |
| 5,061,273 A | 10/1991 | Yock |
| 5,062,827 A | 11/1991 | Wiksell ................ 604/22 |
| 5,064,765 A | 11/1991 | Karasikov et al. |
| 5,069,664 A | 12/1991 | Guess et al. |
| 5,076,276 A | 12/1991 | Sakurai et al. |
| 5,085,635 A * | 2/1992 | Cragg ................ 604/102.03 |
| 5,102,403 A | 4/1992 | Alt |
| 5,106,741 A | 4/1992 | Marotti et al. |
| 5,108,238 A | 4/1992 | Ewing |
| 5,109,830 A | 5/1992 | Cho |
| 5,112,300 A | 5/1992 | Ureche ................ 604/22 |
| 5,116,343 A | 5/1992 | Ams et al. ................ 606/128 |
| 5,122,122 A | 6/1992 | Allgood |
| 5,123,903 A | 6/1992 | Quaid et al. |
| 5,127,405 A | 7/1992 | Alcala et al. |
| 5,129,914 A | 7/1992 | Choi |
| 5,139,496 A | 8/1992 | Hed ................ 606/23 |
| 5,139,509 A | 8/1992 | Fischer et al. |
| 5,147,316 A | 9/1992 | Castillenti |
| 5,151,085 A | 9/1992 | Sakurai et al. |
| 5,151,099 A | 9/1992 | Young et al. |
| 5,152,200 A | 10/1992 | Kaplan |
| 5,152,748 A | 10/1992 | Chastagner |
| 5,156,143 A | 10/1992 | Bocquet et al. |
| 5,156,144 A * | 10/1992 | Iwasaki et al. ................ 601/4 |
| 5,163,421 A | 11/1992 | Bernstein et al. ................ 128/24.1 |
| 5,167,619 A | 12/1992 | Wuchinich ................ 604/22 |
| 5,169,386 A | 12/1992 | Becker et al. |
| 5,171,387 A | 12/1992 | Wuchinich ................ 156/73.3 |
| 5,175,492 A | 12/1992 | Wong et al. |
| 5,176,141 A | 1/1993 | Bom et al. |
| 5,176,677 A | 1/1993 | Wuchinich ................ 604/356 |
| 5,180,363 A | 1/1993 | Idemoto et al. ................ 202/32 |
| 5,190,517 A | 3/1993 | Zieve et al. ................ 604/22 |
| 5,193,525 A | 3/1993 | Silverstein et al. |
| 5,195,955 A | 3/1993 | Don Michael |
| 5,201,315 A | 4/1993 | Griffith |
| 5,201,316 A | 4/1993 | Pomeranz et al. |
| 5,203,338 A | 4/1993 | Jang |
| 5,209,719 A | 5/1993 | Baruch et al. |
| 5,217,465 A | 6/1993 | Steppe |
| 5,221,282 A | 6/1993 | Wuchinich ................ 606/99 |
| 5,222,937 A | 6/1993 | Kagawa |
| 5,222,974 A | 6/1993 | Kensey et al. |
| 5,231,080 A | 7/1993 | Scholkens |
| 5,231,994 A | 8/1993 | Harmjanz |
| 5,232,451 A | 8/1993 | Freitas et al. |
| 5,235,964 A | 8/1993 | Abenaim |
| 5,240,437 A | 8/1993 | Christian |
| 5,243,997 A | 9/1993 | Uflacker et al. ................ 600/565 |
| 5,248,296 A | 9/1993 | Alliger |
| 5,249,580 A | 10/1993 | Griffith |
| 5,255,551 A | 10/1993 | Vetter |
| 5,255,669 A | 10/1993 | Kubota et al. |
| 5,261,805 A | 11/1993 | Gates |
| 5,261,877 A | 11/1993 | Fine et al. |
| 5,263,928 A | 11/1993 | Trauthen et al. |
| 5,263,932 A | 11/1993 | Jang |
| 5,267,954 A | 12/1993 | Nita ................ 604/22 |
| 5,267,958 A | 12/1993 | Buchbinder et al. |
| 5,267,982 A | 12/1993 | Sylvanowicz |
| 5,269,297 A | 12/1993 | Weng et al. ................ 606/128 |
| 5,271,735 A | 12/1993 | Greenfield et al. ................ 604/266 |
| 5,274,297 A | 12/1993 | Hermann et al. |
| 5,285,795 A | 2/1994 | Ryan et al. |
| 5,287,775 A | 2/1994 | Moore |
| 5,290,229 A | 3/1994 | Paskar |

(56) References Cited

U.S. PATENT DOCUMENTS

| | | | |
|---|---|---|---|
| 5,300,021 A | 4/1994 | Wuchinich | 604/22 |
| 5,300,032 A | 4/1994 | Hibbs et al. | |
| 5,300,085 A | 4/1994 | Yock | |
| 5,304,115 A | 4/1994 | Pflueger et al. | 604/22 |
| 5,304,131 A | 4/1994 | Paskar | |
| 5,304,199 A | 4/1994 | Myers | |
| 5,306,261 A | 4/1994 | Alliger et al. | |
| 5,307,816 A | 5/1994 | Hashimoto et al. | |
| 5,311,858 A | 5/1994 | Adair | |
| 5,312,328 A | 5/1994 | Nita et al. | 604/22 |
| 5,312,329 A | 5/1994 | Beaty et al. | 604/22 |
| 5,312,427 A | 5/1994 | Shturman | |
| 5,315,996 A | 5/1994 | Lundquist | |
| 5,318,528 A | 6/1994 | Heaven et al. | |
| 5,319,278 A | 6/1994 | Myohga et al. | |
| 5,323,902 A | 6/1994 | Palmer et al. | |
| 5,324,255 A | 6/1994 | Passafaro et al. | 604/22 |
| 5,324,299 A | 6/1994 | Davison et al. | 606/167 |
| 5,325,698 A | 7/1994 | Nagpal et al. | |
| 5,326,342 A | 7/1994 | Pflueger et al. | |
| 5,329,927 A | 7/1994 | Gardineer et al. | |
| 5,330,444 A | 7/1994 | Webler et al. | |
| 5,330,482 A | 7/1994 | Gibbs et al. | |
| 5,330,497 A | 7/1994 | Freitas et al. | |
| 5,331,242 A | 7/1994 | Petri | |
| 5,334,160 A | 8/1994 | Ellis | |
| 5,334,167 A | 8/1994 | Cocanower | |
| 5,334,183 A | 8/1994 | Wuchinich | 606/46 |
| 5,336,184 A | 8/1994 | Teirstein | |
| 5,336,234 A | 8/1994 | Vigil et al. | |
| 5,336,699 A | 8/1994 | Cooke et al. | |
| 5,342,292 A | 8/1994 | Nita et al. | 604/22 |
| 5,344,395 A | 9/1994 | Whalen et al. | |
| 5,350,395 A | 9/1994 | Yock | |
| 5,351,679 A | 10/1994 | Mayzels et al. | |
| 5,353,798 A | 10/1994 | Sieben | |
| 5,356,385 A | 10/1994 | Latini | |
| 5,356,421 A | 10/1994 | Castro | |
| 5,358,505 A | 10/1994 | Wuchinich | 606/99 |
| 5,362,309 A | 11/1994 | Carter | |
| 5,366,490 A | 11/1994 | Edwards et al. | 607/99 |
| 5,366,899 A | 11/1994 | Shabalin et al. | |
| 5,368,557 A | 11/1994 | Nita et al. | |
| 5,368,558 A | 11/1994 | Nita | 604/22 |
| 5,370,602 A | 12/1994 | Kepley | |
| 5,380,273 A | 1/1995 | Dubrul et al. | |
| 5,380,274 A | 1/1995 | Nita | 604/22 |
| 5,382,228 A | 1/1995 | Nita et al. | 604/22 |
| 5,385,372 A | 1/1995 | Utterberg | |
| 5,387,190 A | 2/1995 | Gotanda et al. | |
| 5,387,197 A | 2/1995 | Smith et al. | |
| 5,388,569 A | 2/1995 | Kepley | |
| 5,390,678 A | 2/1995 | Gesswein et al. | |
| 5,391,144 A | 2/1995 | Sakurai et al. | 604/22 |
| 5,396,902 A | 3/1995 | Brennen et al. | |
| 5,397,293 A | 3/1995 | Alliger et al. | 601/2 |
| 5,397,301 A | 3/1995 | Pflueger et al. | 604/22 |
| 5,402,799 A | 4/1995 | Colon et al. | |
| 5,403,324 A | 4/1995 | Ciervo et al. | |
| 5,405,318 A | 4/1995 | Nita | 604/22 |
| 5,405,341 A | 4/1995 | Martin | |
| 5,406,503 A | 4/1995 | Williams, Jr. et al. | |
| 5,409,112 A | 4/1995 | Sagstetter | |
| 5,417,654 A | 5/1995 | Kelman | 604/22 |
| 5,417,672 A | 5/1995 | Nita et al. | 604/533 |
| 5,419,761 A | 5/1995 | Narayanan et al. | |
| 5,421,338 A | 6/1995 | Crowley et al. | |
| 5,421,829 A | 6/1995 | Olichney et al. | |
| 5,423,797 A | 6/1995 | Adrian et al. | |
| 5,423,838 A | 6/1995 | Willard | |
| 5,425,704 A | 6/1995 | Sakurai et al. | |
| 5,427,118 A | 6/1995 | Nita et al. | 128/772 |
| 5,429,136 A | 7/1995 | Milo et al. | |
| 5,431,664 A | 7/1995 | Ureche et al. | |
| 5,434,827 A | 7/1995 | Bolorforosh | |
| 5,443,443 A | 8/1995 | Shiber | |
| 5,443,456 A | 8/1995 | Alliger et al. | |
| 5,443,457 A | 8/1995 | Ginn et al. | |
| 5,443,468 A | 8/1995 | Johnson | |
| 5,445,617 A | 8/1995 | Yoon | |
| 5,447,509 A | 9/1995 | Mills et al. | 606/1 |
| 5,449,369 A | 9/1995 | Imran | |
| 5,451,233 A | 9/1995 | Yock | |
| 5,452,611 A | 9/1995 | Jones et al. | |
| 5,454,373 A | 10/1995 | Koger et al. | |
| 5,458,584 A | 10/1995 | Ginn et al. | |
| 5,458,612 A | 10/1995 | Chin | 606/192 |
| 5,460,595 A | 10/1995 | Hall et al. | |
| 5,462,530 A | 10/1995 | Jang | |
| 5,464,016 A | 11/1995 | Nicholas et al. | |
| 5,464,409 A | 11/1995 | Mohajer | |
| 5,464,438 A | 11/1995 | Menaker | |
| 5,467,674 A | 11/1995 | Thorn | |
| 5,469,853 A | 11/1995 | Law et al. | |
| 5,470,322 A | 11/1995 | Horzewski et al. | |
| 5,472,441 A | 12/1995 | Edwards et al. | 606/41 |
| 5,474,075 A | 12/1995 | Goldberg et al. | |
| 5,474,530 A | 12/1995 | Passafaro et al. | |
| 5,474,531 A * | 12/1995 | Carter | 604/22 |
| 5,478,353 A | 12/1995 | Yoon | |
| 5,478,558 A | 12/1995 | Eibl et al. | |
| 5,484,398 A | 1/1996 | Stoddard | 604/22 |
| 5,492,001 A | 2/1996 | Sasaki et al. | |
| 5,498,236 A | 3/1996 | Dubrul et al. | 604/22 |
| 5,501,227 A | 3/1996 | Yock | |
| 5,505,714 A | 4/1996 | Dassa et al. | |
| 5,507,738 A | 4/1996 | Ciervo | |
| 5,512,037 A | 4/1996 | Russell et al. | |
| 5,516,043 A | 5/1996 | Manna et al. | 239/102.2 |
| 5,524,620 A | 6/1996 | Rosenschein | |
| 5,524,635 A | 6/1996 | Uflacker et al. | |
| 5,527,273 A | 6/1996 | Manna et al. | |
| 5,527,279 A | 6/1996 | Imran | |
| 5,531,664 A | 7/1996 | Adachi et al. | |
| 5,536,250 A | 7/1996 | Klein et al. | |
| 5,540,656 A | 7/1996 | Pflueger et al. | |
| 5,542,917 A | 8/1996 | Nita et al. | |
| 5,549,563 A | 8/1996 | Kronner | |
| 5,549,576 A | 8/1996 | Patterson et al. | |
| 5,562,620 A | 10/1996 | Klein et al. | |
| 5,569,276 A | 10/1996 | Jang et al. | |
| 5,571,014 A | 11/1996 | Gregory, Jr. et al. | |
| 5,571,085 A | 11/1996 | Accisano, III | |
| 5,575,772 A | 11/1996 | Lennox | |
| 5,580,962 A | 12/1996 | Eibl et al. | |
| 5,582,588 A | 12/1996 | Sakurai et al. | |
| 5,588,432 A | 12/1996 | Crowley | |
| 5,590,653 A | 1/1997 | Aida et al. | |
| 5,593,394 A | 1/1997 | Kanesaka et al. | |
| 5,599,326 A | 2/1997 | Carter | |
| 5,603,445 A | 2/1997 | Hill et al. | 228/4.5 |
| 5,607,404 A | 3/1997 | Khairkhahan | |
| 5,607,440 A | 3/1997 | Danks et al. | |
| 5,611,807 A | 3/1997 | O'Boyle | |
| 5,622,170 A | 4/1997 | Schulz | |
| 5,628,743 A | 5/1997 | Cimino | 606/1 |
| 5,630,427 A | 5/1997 | Hastings | |
| 5,630,797 A | 5/1997 | Diedrich et al. | |
| 5,630,837 A * | 5/1997 | Crowley | 601/2 |
| 5,647,846 A | 7/1997 | Berg et al. | |
| 5,651,364 A | 7/1997 | Yock | |
| 5,651,776 A | 7/1997 | Appling et al. | |
| 5,662,620 A | 9/1997 | Lieber et al. | |
| 5,666,970 A | 9/1997 | Smith | |
| 5,669,881 A | 9/1997 | Dunshee | |
| 5,672,172 A | 9/1997 | Zupkas | 606/20 |
| 5,676,011 A | 10/1997 | Allison | |
| 5,676,649 A | 10/1997 | Boukhny et al. | |
| 5,681,296 A | 10/1997 | Ishida | |
| 5,685,312 A | 11/1997 | Yock | |
| 5,687,474 A | 11/1997 | Hamzehdoost et al. | |
| 5,688,235 A | 11/1997 | Sakurai et al. | |
| 5,690,611 A | 11/1997 | Swartz et al. | |
| 5,693,029 A | 12/1997 | Leonhardt | |

(56) References Cited

U.S. PATENT DOCUMENTS

| | | | |
|---|---|---|---|
| 5,704,787 A | 1/1998 | Hickok et al. | |
| 5,707,359 A | 1/1998 | Bufalini | |
| 5,709,120 A | 1/1998 | Shilling | |
| 5,713,363 A | 2/1998 | Seward et al. | |
| 5,713,848 A | 2/1998 | Dubrul et al. | 604/22 |
| 5,715,825 A | 2/1998 | Crowley | |
| 5,720,300 A | 2/1998 | Fagan et al. | |
| 5,720,710 A | 2/1998 | Tachibana et al. | 601/2 |
| 5,722,627 A | 3/1998 | Hoshino | |
| 5,725,494 A | 3/1998 | Brisken | 604/22 |
| 5,728,062 A | 3/1998 | Brisken | 604/22 |
| 5,735,811 A | 4/1998 | Brisken | 604/22 |
| 5,741,225 A | 4/1998 | Lax et al. | 604/22 |
| 5,749,889 A | 5/1998 | Bacich et al. | |
| 5,749,914 A | 5/1998 | Janssen | |
| 5,752,932 A | 5/1998 | Ellis et al. | |
| 5,758,420 A | 6/1998 | Schmidt et al. | |
| 5,765,418 A | 6/1998 | Rosenberg | |
| 5,769,868 A | 6/1998 | Yock | |
| 5,772,627 A | 6/1998 | Acosta et al. | 604/22 |
| 5,775,328 A | 7/1998 | Lowe et al. | |
| 5,776,065 A | 7/1998 | Mehmanpazir et al. | |
| 5,782,861 A | 7/1998 | Cragg et al. | |
| 5,797,920 A | 8/1998 | Kim | |
| 5,803,083 A | 9/1998 | Buck et al. | |
| 5,810,860 A | 9/1998 | Adrian | |
| 5,813,998 A | 9/1998 | Dias | |
| 5,824,042 A | 10/1998 | Lombardi et al. | |
| 5,827,203 A | 10/1998 | Nita | 601/2 |
| 5,827,229 A | 10/1998 | Auth et al. | |
| 5,830,125 A | 11/1998 | Scribner et al. | |
| 5,830,127 A | 11/1998 | DeCastro | 600/157 |
| 5,830,195 A | 11/1998 | Peters et al. | |
| 5,833,644 A | 11/1998 | Zadno-Azizi et al. | |
| 5,833,650 A | 11/1998 | Imran | |
| 5,836,306 A | 11/1998 | Duane et al. | |
| 5,836,896 A | 11/1998 | Rosenschein | 601/2 |
| 5,836,897 A | 11/1998 | Sakuri et al. | 601/2 |
| 5,840,027 A | 11/1998 | Swartz et al. | |
| 5,840,031 A | 11/1998 | Crowley | |
| 5,840,151 A | 11/1998 | Munsch | |
| 5,843,017 A | 12/1998 | Yoon | 604/22 |
| 5,846,218 A | 12/1998 | Brisken et al. | 604/22 |
| 5,849,009 A | 12/1998 | Bernaz | |
| 5,861,023 A | 1/1999 | Vachon | |
| 5,868,773 A | 2/1999 | Danks et al. | |
| 5,868,778 A | 2/1999 | Gershony et al. | |
| 5,875,782 A | 3/1999 | Ferrari et al. | |
| 5,882,329 A * | 3/1999 | Patterson et al. | 604/500 |
| 5,882,347 A | 3/1999 | Mouris-Laan et al. | |
| 5,890,406 A | 4/1999 | Thorn | |
| 5,891,149 A | 4/1999 | Young et al. | 606/80 |
| 5,895,370 A | 4/1999 | Edwards et al. | 604/22 |
| 5,895,997 A | 4/1999 | Puskas et al. | |
| 5,897,557 A | 4/1999 | Chin et al. | |
| 5,897,569 A | 4/1999 | Kellogg et al. | |
| 5,902,289 A | 5/1999 | Swartz et al. | |
| 5,904,670 A | 5/1999 | Schreiner | |
| 5,906,628 A | 5/1999 | Miyawaki et al. | |
| 5,908,381 A | 6/1999 | Aznoian et al. | |
| 5,910,129 A | 6/1999 | Koblish et al. | |
| 5,916,192 A | 6/1999 | Nita et al. | 604/22 |
| 5,916,210 A | 6/1999 | Winston | |
| 5,919,163 A | 7/1999 | Glickman | |
| 5,919,174 A | 7/1999 | Hanson | |
| 5,920,395 A | 7/1999 | Schulz | |
| 5,921,915 A | 7/1999 | Aznoian et al. | |
| 5,925,016 A | 7/1999 | Chornenky et al. | |
| 5,928,218 A | 7/1999 | Gelbfish | 604/540 |
| 5,931,805 A | 8/1999 | Brisken | 604/22 |
| 5,935,096 A | 8/1999 | Barrett | 604/22 |
| 5,935,142 A | 8/1999 | Hood | 606/169 |
| 5,935,143 A | 8/1999 | Hood | |
| 5,944,687 A | 8/1999 | Benett et al. | |
| 5,951,480 A | 9/1999 | White et al. | |
| 5,951,539 A | 9/1999 | Nita et al. | |
| 5,951,583 A | 9/1999 | Jensen et al. | |
| 5,957,882 A | 9/1999 | Nita et al. | 604/22 |
| 5,961,444 A | 10/1999 | Thompson | |
| 5,964,756 A | 10/1999 | McGaffigan et al. | 606/41 |
| 5,971,949 A | 10/1999 | Levin et al. | 604/22 |
| 5,971,960 A | 10/1999 | Flom et al. | |
| 5,971,983 A | 10/1999 | Lesh | |
| 5,974,884 A | 11/1999 | Sano et al. | |
| 5,976,093 A | 11/1999 | Jang | |
| 5,980,563 A | 11/1999 | Tu et al. | |
| 5,981,444 A | 11/1999 | Sawada et al. | |
| 5,984,882 A | 11/1999 | Rosenschein et al. | |
| 5,984,950 A | 11/1999 | Cragg et al. | |
| 5,987,349 A | 11/1999 | Schulz | |
| 5,989,208 A | 11/1999 | Nita | 604/22 |
| 5,989,209 A | 11/1999 | Barrett | 604/22 |
| 5,989,274 A | 11/1999 | Davison et al. | 606/169 |
| 5,993,408 A | 11/1999 | Zaleski | |
| 5,997,497 A | 12/1999 | Nita et al. | |
| 5,997,523 A | 12/1999 | Jang | |
| 6,001,355 A | 12/1999 | Dowdle | |
| 6,004,269 A | 12/1999 | Crowley et al. | |
| 6,007,499 A * | 12/1999 | Martin et al. | 601/3 |
| 6,007,514 A | 12/1999 | Nita | |
| 6,010,476 A | 1/2000 | Saadat | |
| 6,010,498 A | 1/2000 | Guglielmi | |
| 6,017,340 A | 1/2000 | Cassidy et al. | |
| 6,017,354 A | 1/2000 | Culp et al. | |
| 6,017,359 A | 1/2000 | Gershony et al. | |
| 6,019,777 A | 2/2000 | Mackenzie | |
| 6,021,694 A | 2/2000 | Beger | |
| 6,022,336 A | 2/2000 | Zadno-Azizi et al. | |
| 6,022,369 A | 2/2000 | Jacobsen et al. | |
| 6,024,718 A | 2/2000 | Chen et al. | |
| 6,027,515 A | 2/2000 | Cimino | |
| 6,032,078 A | 2/2000 | Rudie | 607/101 |
| 6,033,375 A * | 3/2000 | Brumbach | 604/22 |
| 6,033,411 A | 3/2000 | Preissman | |
| 6,036,671 A | 3/2000 | Frey | |
| 6,036,697 A | 3/2000 | DiCaprio | |
| 6,036,715 A | 3/2000 | Yock | |
| 6,039,693 A | 3/2000 | Seward et al. | |
| 6,039,762 A | 3/2000 | McKay | |
| 6,045,527 A | 4/2000 | Appelbaum et al. | |
| 6,048,329 A | 4/2000 | Thompson et al. | |
| 6,050,949 A | 4/2000 | White et al. | |
| 6,051,772 A | 4/2000 | Cameron et al. | |
| 6,053,904 A | 4/2000 | Scribner et al. | |
| RE36,693 E | 5/2000 | Reich | |
| 6,056,722 A | 5/2000 | Jayaraman | |
| 6,057,798 A | 5/2000 | Burrier et al. | |
| 6,059,789 A | 5/2000 | Dinger et al. | |
| 6,062,001 A | 5/2000 | Kunik | |
| 6,062,059 A | 5/2000 | Feldcamp | |
| 6,068,610 A | 5/2000 | Ellis et al. | |
| 6,077,285 A | 6/2000 | Boukhny | 606/169 |
| 6,083,191 A | 7/2000 | Rose | |
| 6,083,501 A | 7/2000 | Miyata et al. | |
| 6,090,118 A | 7/2000 | McGuckin, Jr. | |
| 6,099,464 A | 8/2000 | Shimizu et al. | |
| 6,106,475 A | 8/2000 | Lowe et al. | |
| 6,106,538 A | 8/2000 | Shiber | |
| 6,107,161 A | 8/2000 | Kitaguro et al. | |
| 6,110,142 A | 8/2000 | Pinchuk et al. | |
| 6,110,176 A | 8/2000 | Shapira | |
| 6,113,558 A | 9/2000 | Rosenschein et al. | |
| 6,113,570 A | 9/2000 | Siegel et al. | |
| 6,113,580 A | 9/2000 | Dolisi | |
| 6,123,718 A | 9/2000 | Tu et al. | |
| 6,124,150 A | 9/2000 | Corisis | |
| 6,124,546 A | 9/2000 | Hayward et al. | |
| 6,124,634 A | 9/2000 | Akram et al. | |
| 6,129,672 A | 10/2000 | Seward et al. | |
| 6,146,380 A | 11/2000 | Racz et al. | |
| 6,146,381 A | 11/2000 | Bowe et al. | |
| 6,156,018 A | 12/2000 | Hassett | |
| 6,159,195 A | 12/2000 | Ha et al. | |
| 6,162,053 A | 12/2000 | Hollander | |

(56) References Cited

U.S. PATENT DOCUMENTS

| | | | |
|---|---|---|---|
| 6,165,197 A | 12/2000 | Yock | |
| 6,190,353 B1 | 2/2001 | Makower et al. | |
| 6,193,683 B1 | 2/2001 | Ludin et al. | |
| 6,200,269 B1 | 3/2001 | Lin et al. | |
| 6,200,315 B1 | 3/2001 | Gaiser et al. | |
| 6,203,516 B1 | 3/2001 | Kepley | |
| 6,203,568 B1 | 3/2001 | Lombardi et al. | |
| 6,224,565 B1 | 5/2001 | Cimino | |
| 6,228,046 B1 | 5/2001 | Brisken | |
| 6,231,514 B1 | 5/2001 | Lowe et al. | |
| 6,231,518 B1 | 5/2001 | Grabek et al. | |
| 6,234,971 B1 | 5/2001 | Jang | |
| 6,235,000 B1 | 5/2001 | Milo et al. | |
| 6,241,703 B1 | 6/2001 | Levin et al. | |
| 6,245,095 B1 | 6/2001 | Dobak, III et al. | |
| 6,247,592 B1 | 6/2001 | Racicot et al. | |
| 6,258,798 B1 | 7/2001 | Wallentin | |
| 6,262,062 B1 | 7/2001 | Clemens | |
| 6,270,460 B1 | 8/2001 | McCartan et al. | |
| 6,277,084 B1 | 8/2001 | Abele et al. | |
| 6,279,743 B1 | 8/2001 | Ballard et al. | |
| 6,280,413 B1 | 8/2001 | Clark et al. | |
| 6,283,951 B1 | 9/2001 | Flaherty et al. | |
| 6,287,271 B1 | 9/2001 | Dubrul et al. | 604/22 |
| 6,287,272 B1 | 9/2001 | Brisken et al. | |
| 6,290,662 B1 | 9/2001 | Morris et al. | |
| 6,290,673 B1 | 9/2001 | Shanley | |
| 6,293,725 B1 | 9/2001 | Winkvist | |
| 6,296,658 B1 | 10/2001 | Gershony et al. | |
| 6,303,635 B1 | 10/2001 | Kawai et al. | |
| 6,306,097 B1 | 10/2001 | Park et al. | |
| 6,307,156 B1 | 10/2001 | Avellanet | |
| 6,309,379 B1 | 10/2001 | Willard et al. | |
| 6,312,406 B1 | 11/2001 | Jayaraman | |
| 6,322,541 B2 | 11/2001 | West et al. | |
| 6,329,778 B1 | 12/2001 | Culp et al. | |
| 6,346,091 B1 | 2/2002 | Jacobsen et al. | |
| 6,348,039 B1 | 2/2002 | Flachman et al. | |
| 6,358,252 B1 | 3/2002 | Shapira | |
| 6,364,840 B1 | 4/2002 | Crowley | |
| 6,364,841 B1 | 4/2002 | White et al. | |
| 6,368,611 B1 | 4/2002 | Whitbourne et al. | |
| 6,376,513 B1 | 4/2002 | Akahane et al. | |
| 6,383,151 B1 | 5/2002 | Diederich et al. | |
| 6,391,042 B1 | 5/2002 | Cimino | |
| 6,396,293 B1 | 5/2002 | Vinther et al. | |
| 6,398,776 B1 | 6/2002 | Sekino et al. | |
| 6,398,792 B1 | 6/2002 | O'Connor | |
| 6,410,560 B1 | 6/2002 | Akahane et al. | |
| 6,416,511 B1 | 7/2002 | Lesh et al. | |
| 6,416,530 B2 | 7/2002 | DeVries et al. | |
| 6,416,737 B1 | 7/2002 | Manolagas et al. | |
| 6,419,644 B1 | 7/2002 | White et al. | |
| 6,433,464 B2 | 8/2002 | Jones | |
| 6,440,726 B1 | 8/2002 | Resnick | |
| 6,440,947 B1 | 8/2002 | Barron et al. | |
| 6,443,903 B1 | 9/2002 | White et al. | |
| 6,450,975 B1 | 9/2002 | Brennan et al. | |
| 6,451,303 B1 | 9/2002 | Whitehouse et al. | |
| 6,454,737 B1 | 9/2002 | Nita et al. | |
| 6,454,757 B1 | 9/2002 | Nita et al. | |
| 6,457,365 B1 | 10/2002 | Stephens et al. | |
| 6,458,375 B1 | 10/2002 | Gertzman et al. | |
| 6,462,172 B1 | 10/2002 | Maclennan et al. | |
| 6,464,660 B2 | 10/2002 | Brisken et al. | |
| 6,469,419 B2 | 10/2002 | Kato et al. | |
| 6,471,656 B1 | 10/2002 | Shalman et al. | |
| 6,475,185 B1 | 11/2002 | Rauker et al. | |
| 6,478,751 B1 | 11/2002 | Krueger et al. | |
| 6,482,218 B1 | 11/2002 | Tran | |
| 6,485,481 B1 | 11/2002 | Pfeiffer | |
| 6,491,710 B2 | 12/2002 | Satake | |
| 6,491,711 B1 | 12/2002 | Durcan | |
| 6,494,883 B1 | 12/2002 | Ferree | |
| 6,494,885 B1 | 12/2002 | Dhindsa | |
| 6,494,891 B1 | 12/2002 | Cornish et al. | |
| 6,494,893 B2 | 12/2002 | Dubrul et al. | |
| 6,497,667 B1 | 12/2002 | Miller et al. | |
| 6,497,698 B1 | 12/2002 | Fonger et al. | |
| 6,503,223 B1 | 1/2003 | Sekido et al. | |
| 6,508,781 B1 | 1/2003 | Brennan et al. | |
| 6,508,782 B1 | 1/2003 | Evans et al. | |
| 6,509,348 B1 | 1/2003 | Ogletree | |
| 6,511,492 B1 | 1/2003 | Rosenbluth et al. | |
| 6,512,957 B1 | 1/2003 | Witte | |
| 6,514,210 B2 | 2/2003 | Ohara et al. | |
| 6,522,929 B2 | 2/2003 | Swing | |
| 6,524,251 B2 * | 2/2003 | Rabiner et al. | 600/439 |
| 6,527,115 B2 | 3/2003 | Rabiner et al. | |
| 6,530,923 B1 | 3/2003 | Dubrul et al. | |
| 6,544,276 B1 | 4/2003 | Azizi | |
| 6,544,279 B1 | 4/2003 | Hopkins et al. | |
| 6,544,541 B1 | 4/2003 | Zahradka | |
| 6,547,724 B1 | 4/2003 | Soble et al. | |
| 6,547,754 B1 | 4/2003 | Evans et al. | |
| 6,551,269 B2 | 4/2003 | Clemens et al. | |
| 6,551,327 B1 | 4/2003 | Dhindsa | |
| 6,551,337 B1 | 4/2003 | Rabiner et al. | 606/169 |
| 6,558,334 B2 | 5/2003 | Shalman et al. | |
| 6,569,109 B2 | 5/2003 | Sakurai et al. | |
| 6,569,148 B2 | 5/2003 | Bagaoisan et al. | |
| 6,572,555 B2 | 6/2003 | White et al. | |
| 6,575,959 B1 | 6/2003 | Sarge et al. | |
| 6,575,993 B1 | 6/2003 | Yock | |
| 6,577,042 B2 | 6/2003 | Lee et al. | |
| 6,579,277 B1 | 6/2003 | Rabiner et al. | 604/525 |
| 6,579,279 B1 | 6/2003 | Rabiner et al. | 604/528 |
| 6,579,302 B2 | 6/2003 | Duerig et al. | |
| 6,585,657 B2 | 7/2003 | Yock | |
| 6,589,253 B1 | 7/2003 | Cornish et al. | |
| 6,592,548 B2 | 7/2003 | Jayaraman | |
| 6,596,020 B2 | 7/2003 | Vardi et al. | |
| 6,605,074 B2 | 8/2003 | Zadno-Azizi et al. | |
| 6,611,793 B1 | 8/2003 | Burnside et al. | |
| 6,615,080 B1 | 9/2003 | Unsworth et al. | |
| 6,617,760 B1 | 9/2003 | Peterson et al. | |
| 6,620,113 B2 | 9/2003 | White et al. | |
| 6,626,853 B2 | 9/2003 | White et al. | |
| 6,626,926 B2 | 9/2003 | Friedman et al. | |
| 6,629,948 B2 | 10/2003 | Rockley et al. | |
| 6,645,149 B1 | 11/2003 | Smith | |
| 6,645,152 B1 | 11/2003 | Jung et al. | |
| 6,647,755 B2 | 11/2003 | Rabiner et al. | 72/291 |
| 6,648,881 B2 | 11/2003 | KenKnight et al. | |
| 6,652,547 B2 | 11/2003 | Rabiner et al. | 606/159 |
| 6,655,386 B1 | 12/2003 | Makower et al. | |
| 6,660,013 B2 | 12/2003 | Rabiner et al. | |
| 6,669,665 B2 | 12/2003 | Jayaraman | |
| 6,679,873 B2 | 1/2004 | Rabiner et al. | 604/528 |
| 6,682,556 B1 | 1/2004 | Ischinger | |
| 6,689,086 B1 | 2/2004 | Nita et al. | |
| 6,689,087 B2 | 2/2004 | Pal et al. | |
| 6,692,460 B1 | 2/2004 | Jayaraman | |
| 6,695,781 B2 | 2/2004 | Rabiner et al. | 600/129 |
| 6,695,782 B2 * | 2/2004 | Ranucci et al. | 600/439 |
| 6,702,748 B1 | 3/2004 | Nita et al. | |
| 6,702,750 B2 | 3/2004 | Yock | |
| 6,712,766 B2 | 3/2004 | Harada | |
| 6,726,698 B2 | 4/2004 | Cimino | |
| D489,973 S | 5/2004 | Root et al. | |
| 6,730,037 B2 | 5/2004 | Jang | |
| 6,730,048 B1 | 5/2004 | Hare et al. | 601/2 |
| 6,733,451 B2 | 5/2004 | Rabiner et al. | 600/439 |
| 6,760,165 B2 | 7/2004 | Wulff et al. | |
| 6,761,690 B2 | 7/2004 | Sakurai et al. | |
| 6,790,204 B2 | 9/2004 | Zadno-Azizi et al. | |
| 6,802,835 B2 | 10/2004 | Rabiner et al. | |
| 6,840,952 B2 | 1/2005 | Saker et al. | |
| 6,849,062 B2 | 2/2005 | Kantor | |
| 6,855,123 B2 | 2/2005 | Nita | |
| 6,855,125 B2 | 2/2005 | Shanley | |
| 6,860,876 B2 | 3/2005 | Chen | |
| 6,866,670 B2 | 3/2005 | Rabiner et al. | |
| 6,878,106 B1 | 4/2005 | Herrmann | |

(56) References Cited

U.S. PATENT DOCUMENTS

| | | | |
|---|---|---|---|
| 6,887,257 B2 | 5/2005 | Salahieh et al. | |
| 6,908,472 B2 | 6/2005 | Wiener et al. | |
| 6,921,411 B2 | 7/2005 | Yock | |
| 6,923,788 B2 | 8/2005 | Kantor | |
| 6,929,632 B2 | 8/2005 | Nita et al. | |
| 6,939,317 B2 | 9/2005 | Zacharias | |
| 6,942,620 B2 | 9/2005 | Nita et al. | |
| 6,942,677 B2 | 9/2005 | Nita et al. | |
| 6,966,891 B2 | 11/2005 | Ookubo et al. | |
| 6,984,220 B2 | 1/2006 | Wuchinich | |
| 7,503,895 B2 * | 3/2009 | Rabiner et al. | 600/439 |
| 2001/0047166 A1 | 11/2001 | Wuchinich | |
| 2002/0007130 A1 | 1/2002 | Burbank et al. | |
| 2002/0016565 A1 | 2/2002 | Zadno-Azizi et al. | |
| 2002/0029014 A1 | 3/2002 | Jayaraman | |
| 2002/0029054 A1 | 3/2002 | Rabiner et al. | |
| 2002/0055754 A1 | 5/2002 | Ranucci et al. | 600/169 |
| 2002/0077550 A1 | 6/2002 | Rabiner et al. | 600/439 |
| 2002/0077643 A1 | 6/2002 | Rabiner et al. | |
| 2002/0082503 A1 | 6/2002 | Chandrasekaran et al. | |
| 2002/0091407 A1 | 7/2002 | Zadno-Azizi et al. | |
| 2002/0095141 A1 | 7/2002 | Belef et al. | |
| 2002/0107446 A1 | 8/2002 | Rabiner et al. | |
| 2003/0009125 A1 | 1/2003 | Nita et al. | |
| 2003/0045835 A1 | 3/2003 | Anderson et al. | |
| 2003/0045887 A1 | 3/2003 | Sakurai et al. | |
| 2003/0048037 A1 | 3/2003 | Boyd | |
| 2003/0074006 A1 | 4/2003 | Mowry et al. | |
| 2003/0114732 A1 | 6/2003 | Webler et al. | |
| 2003/0120208 A1 | 6/2003 | Houser et al. | |
| 2003/0125751 A1 | 7/2003 | Griffin et al. | |
| 2003/0176791 A1 | 9/2003 | Rabiner et al. | 600/439 |
| 2003/0181923 A1 | 9/2003 | Vardi | |
| 2003/0197958 A1 | 10/2003 | Wulff et al. | |
| 2003/0212331 A1 | 11/2003 | Fenton et al. | |
| 2003/0225332 A1 | 12/2003 | Okada et al. | |
| 2003/0236539 A1 | 12/2003 | Rabiner et al. | |
| 2004/0019266 A1 | 1/2004 | Marciante et al. | |
| 2004/0024393 A1 | 2/2004 | Nita et al. | |
| 2004/0024402 A1 | 2/2004 | Nita | |
| 2004/0039311 A1 | 2/2004 | Nita et al. | |
| 2004/0039375 A1 | 2/2004 | Miyazawa | |
| 2004/0059227 A1 | 3/2004 | Nita et al. | |
| 2004/0059280 A1 | 3/2004 | Makower et al. | |
| 2004/0068189 A1 | 4/2004 | Wilson et al. | |
| 2004/0097996 A1 | 5/2004 | Rabiner et al. | |
| 2004/0106866 A1 | 6/2004 | Ookubo et al. | |
| 2004/0119287 A1 | 6/2004 | Williams et al. | |
| 2004/0138570 A1 | 7/2004 | Nita et al. | |
| 2004/0158150 A1 | 8/2004 | Rabiner et al. | 600/439 |
| 2004/0167507 A1 | 8/2004 | Nita et al. | |
| 2004/0199228 A1 | 10/2004 | Wilson | |
| 2004/0204670 A1 | 10/2004 | Nita et al. | |
| 2004/0204729 A1 | 10/2004 | Cimino | |
| 2004/0210140 A1 | 10/2004 | Rabiner et al. | |
| 2004/0213866 A1 | 10/2004 | Wulff et al. | |
| 2004/0243052 A1 | 12/2004 | Kauphusman et al. | |
| 2005/0043629 A1 | 2/2005 | Rabiner et al. | |
| 2005/0059991 A1 | 3/2005 | Shanley | |
| 2005/0070794 A1 | 3/2005 | Deal et al. | |
| 2005/0101870 A1 | 5/2005 | Yamaguchi et al. | |
| 2005/0101906 A1 | 5/2005 | Nita | |
| 2005/0113688 A1 | 5/2005 | Nita et al. | |
| 2005/0119606 A1 | 6/2005 | Nita | |
| 2005/0124877 A1 | 6/2005 | Nita et al. | |
| 2005/0171570 A1 | 8/2005 | Yock | |
| 2005/0209677 A1 | 9/2005 | Shaked | |
| 2005/0240165 A1 | 10/2005 | Miki et al. | |
| 2005/0245951 A1 | 11/2005 | Nita et al. | |
| 2005/0277577 A1 | 12/2005 | Hunter et al. | |
| 2005/0283080 A1 | 12/2005 | Nita et al. | |

FOREIGN PATENT DOCUMENTS

| | | | |
|---|---|---|---|
| CA | 2 362 689 | 9/2000 | |
| DE | 428980 | 5/1926 | |
| DE | 203 229 | 10/1983 | |
| DE | 37 31 482 | 4/1988 | |
| EP | 0 121 491 | 10/1984 | |
| EP | 0 243 298 | 10/1987 | |
| EP | 0293472 | 12/1988 | A61B 17/22 |
| EP | 0 316 796 | 5/1989 | |
| EP | 0 353 294 | 2/1990 | |
| EP | 0421285 | 4/1991 | |
| EP | 0 493 047 | 7/1992 | |
| EP | 0 542 103 | 5/1993 | |
| EP | 0541249 | 5/1993 | |
| EP | 0 891 744 | 1/1999 | |
| FR | 461395 | 12/1913 | |
| FR | 2 614 524 | 11/1988 | |
| GB | 19559 | 0/1899 | |
| GB | 1 371 335 | 10/1974 | |
| GB | 2 032 221 | 4/1980 | |
| GB | 2 325 192 | 11/1998 | |
| JP | 63-305856 A | 12/1988 | |
| JP | 1-288249 A | 11/1989 | |
| JP | 08-117240 A | 5/1996 | |
| WO | WO 87/01276 | 3/1987 | |
| WO | WO 89/06515 | 7/1989 | |
| WO | WO 90/01300 | 2/1990 | A61B 17/32 |
| WO | WO 90/10423 | 9/1990 | |
| WO | WO 91/07138 | 5/1991 | |
| WO | WO 92/04071 | 3/1992 | |
| WO | WO 92/11815 | 7/1992 | |
| WO | WO 93/16646 | 9/1993 | |
| WO | WO 95/03740 | 2/1995 | A61B 17/20 |
| WO | WO 96/07377 | 3/1996 | |
| WO | WO 96/29935 | 10/1996 | |
| WO | WO 9809571 | 3/1998 | |
| WO | WO 8/35721 | 8/1998 | |
| WO | WO 98/40021 | 9/1998 | |
| WO | WO 98/55032 | 12/1998 | |
| WO | WO 99/16360 | 4/1999 | |
| WO | WO 99/33404 | 7/1999 | |
| WO | WO 99/35982 | 7/1999 | |
| WO | WO 99/39647 | 8/1999 | |
| WO | WO 22/21444 | 4/2000 | A61B 17/20 |
| WO | WO 00/53263 | 9/2000 | |
| WO | WO 0053341 | 9/2000 | |
| WO | WO 0124716 | 4/2001 | |
| WO | WO 0213678 | 2/2002 | |

OTHER PUBLICATIONS

Beckenbaugh, R.D. and M.S. Ilstrup, *Total Hip Arthoplasty*, J. Bone and Joint Surgery, vol. 60A, pp. 308-314 (1978).

Brochure, Endo-Urology—A Breakthrough in Ultrasonic Lithotripsy, Karl Storz Endoscopy-America, Inc. (1984).

Brochure, Instruments and Apparatus for Lithotripsy, Richard Wolf GmbH, Knittlinger, West Germany (1984).

Brochure, Percutaneous Low Pressure Universal Nephroscope, Richard Wolf, Knittlinger, West Germany (1984).

Brochure, *Sonic Surgery System*, Quintron, Inc.

Cameron, Proximal Femoral Osteotomy in Difficult Revision Hip Surgery: How to Revise the Unrevisable, 18 Contemp. Orthopaedics 565 (1989).

Casper, Current Development of Instrumentation for Arthroscopy, *Clinics in Sports Medicine*, 6:3 (1987), pp. 626-627.

Chaussy et al., "Transurethral Ultrasonic Ureterolithotripsy Using a Solid-Wire Probe," *Urology*, 29(5):531-532 (May 1987).

De Puy Inc., Catalog (1966).

Eisner, Physical Acoustics, 1964, pp. 353-363.

Emsinger, Ultrasonics, 1988, pp. 419-492.

Ensminger, *Ultrasonics: Fundamentals, Technology, Applications*, pp. 462-467, Marcel Dekker Inc. (1988).

Epstein et al., Surgical Management of Extensive Intramedullary Spinal Cord Astrocytoma in Children, Concepts in Pediatric Neurosurgery, 2, (1982) pp. 29-44.

(56) References Cited

OTHER PUBLICATIONS

Goliamina, "*Ultrasonic Surgery*". Proceedings of the Eighth Int'l. Cong. on Acoustics, London, 1974, pp. 63-69.
Gray, "Endovascular treatment of peripheral arterial disease," "*Journal of the American Osteopathic Assocation*, 100(10):S15-S20 (Supplement to October 2000).
Harris et al., A New Technique for Removal of Broken Femoral Stems in Total Hip Replacement, 63-A J. Bone & Joint Surgery 842 (1981).
Johnson, Arthroscopic Surgery: Principles and Practice (3rd Edition), Verlag Springer (1986), pp. 244-245.
Karpman et al., The Lithotriptor and Its Potential Use in the Revision of Total Hip Athroplasty, 16 Orthopaedic Rev. 81 (1987).
Klapper and Caillouette, "*The Use of Ultrasonic Tools in Revision Arthoplasty Procedures*", 20:3 Contemporary Orthopaedics, pp. 273-279 (March 1990).
Krawitt et al., Ultrasonic Aspiration of Prostate, Bladder Tumors and Stones, *Urology*, 30:6 (1987) pp. 578-580.
Lin, Posterior Lumbar Inerbody Fusion Technique: Complications and Pitfalls, 193 Clinical Orthopaedics and Related Research 90 (1985).
Malloy et al., Endoscopis Ultrasonic Aspiration of the Prostate, Bladder Tumors and Stones, Journal of Urology Supplement, May 1989.
Malloy et al., Transurethral Ultrasonic Aspiration of the Prostate, A.U.A., May 1989.
McClelland et al., Atraumatic Removal of a Well-Fixed Porous Ingrowth Hip Prosthesis, 15 Orthopaedic Rev. 75 (1986).
Moreland et al., *Techniques for Removal of Prosthesis and Cement in Total Hip Revisional Surgery*, Contemporary Orthopaedics, V. 21, No. 6, pp. 595-635, 1990.
Moreland et al., The Window Technique for the Removal of Broken Femoral Stems in Total Hip Replacement, 212 Clinical Orhtopaedics and Related Research 245 (1986).
Neppiras, The Pre-Stressed Piezoelectric Sandwich Transducer, 1973, pp. 295-302.
Rayleigh, The Theory of Sound, vol. 1, 1894, pp. 255-305.
Richards Mfg. Co., Orthopedic Catalog (1981).
Richmond et al., Evaluation of the Histopathology of Brain Tumor Tisue Obtained by Ultrasonic Aspiration, *Neurosurgery*, 13:4 (1983), pp. 415-419.
Rozenberg, Sources of High-Instensity Ultrasound, vol. 2, 1973, pp. 111-114.
Sahagian, Richard, "Critical Insight: Making Devices with Radiopaque Coatings," May 1999, *Medical Device & Diagnostic Industry Magazine*(http://www.devicelink.com/mddi/archive/99/05/011.html).
Schwartz, Jr. et al., Femoral Fracture During Non-Cemented Total Hip Arthroplasty, 71-A J. Bone & Joint Surgery 1135 (1989).
Sternlieb et al., Ultrasonic Restoration of Severely Calcified Aortic Valve, *The Lancet*, Aug. 20, 1988, p. 446.
Weis, Jr., A Sonic Tool for Spinal Fusion, & Orthopedic Clinics of North Am. 43 (1977).
Wick et al., "Tool and Manufacturing Engineers Handbood," Fourth Edition, vol. II, Forming, Society of Manufacturing Engineers, Michigan, 1983-1984, pp. 13-1 through 13-2.
Zhou et al., Effect of Press-Fit Femoral Stems on Strains in the Femur, 5 J. Arthoplasty 71 (1990).
International Search Report: PCT/US04/04379, Jun. 17, 2005.
International Search Report: PCT/US03/09163, Oct. 8, 2003.
International Search Report based on PCT/US02/02059 dated Jul. 9, 2002.
International Search Report based on PCT/US03/09163 dated Oct. 8, 2003.

\* cited by examiner

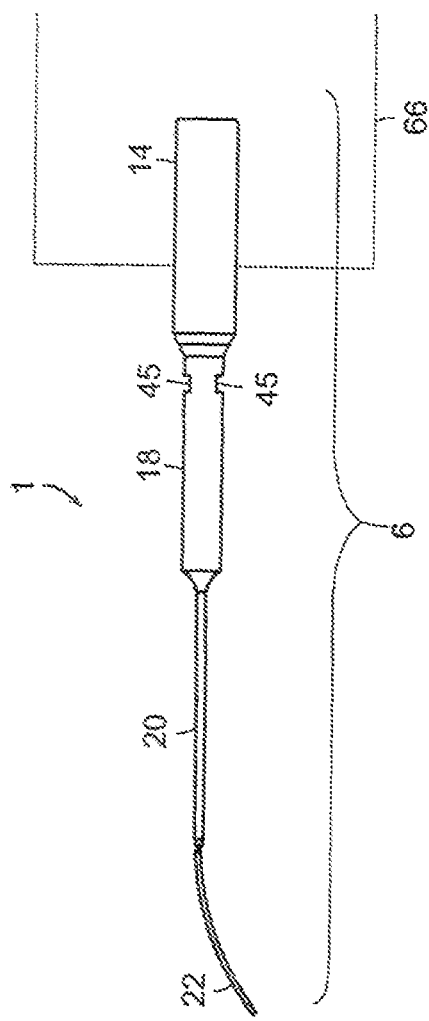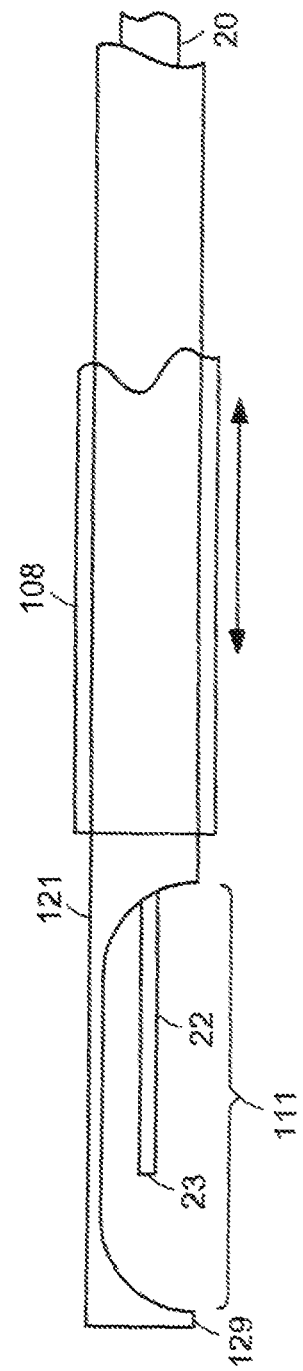

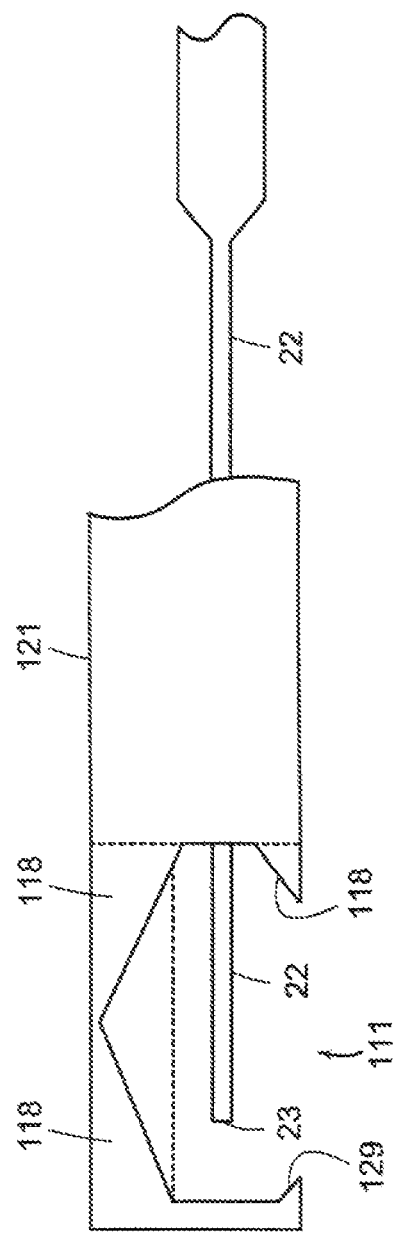

MEDICAL SYSTEMS AND RELATED METHODS

RELATED APPLICATIONS

Continuation of application Ser. No. 10/665,445, now abandoned, filed Sep. 19, 2003, which is a continuation of application Ser. No. 09/776,015, filed Feb. 2, 2001, now U.S. Pat. No. 6,652,547, which is a continuation-in-part of application Ser. No. 09/618,352, filed Jul. 19, 2000, now U.S. Pat. No. 6,551,337.

FIELD OF THE INVENTION

The present invention relates generally to medical systems and related methods.

BACKGROUND OF THE INVENTION

Vascular occlusions (clots or thrombi and occlusional deposits, such as calcium, fatty deposits, or plaque), result in the restriction or blockage of blood flow in the vessels in which they occur. Occlusions result in oxygen deprivation ("ischemia") of tissues supplied by these blood vessels. Prolonged ischemia results in permanent damage of tissues which can lead to myocardial infarction, stroke, or death. Targets for occlusion include coronary arteries, peripheral arteries and other blood vessels. The disruption of an occlusion or thrombolysis can be effected by pharmacological agents and/or or mechanical means. However, many thrombolytic drugs are associated with side effects such as severe bleeding which can result in cerebral hemorrhage. Mechanical methods of thrombolysis include balloon angioplasty, which can result in ruptures in a blood vessel, and is generally limited to larger blood vessels. Scarring of vessels is common, which may lead to the formation of a secondary occlusion (a process known as restenosis). Another common problem is secondary vasoconstriction (classic recoil), a process by which spasms or abrupt closure of the vessel occurs. These problems are common in treatments employing interventional devices. In traditional angioplasty, for instance, a balloon catheter is inserted into the occlusion, and through the application of hydraulic forces in the range of ten to fourteen atmospheres of pressure, the balloon is inflated. The non-compressible balloon applies this significant force to compress and flatten the occlusion, thereby operating the vessel for blood flow. However, these extreme forces result in the application of extreme stresses to the vessel, potentially rupturing the vessel, or weaking it thereby increasing the chance of post-operative aneurysm, or creating vasoconstrictive or restenotic conditions. In addition, the particulate matter isn't removed, rather it is just compressed. Other mechanical devices that drill through and attempt to remove an occlusion have also been used, and create the same danger of physical damage to blood vessels.

Ultrasonic probes are devices which use ultrasonic energy to fragment body tissue (see, e.g., U.S. Pat. Nos. 5,112,300; 5,180,363; 4,989,583; 4,931,047; 4,922,902; and 3,805,787) and have been used in many surgical procedures. The use of ultrasonic energy has been proposed both to mechanically disrupt clots, and to enhance the intravascular delivery of drugs to clot formations (see, e.g., U.S. Pat. Nos. 5,725,494; 5,728,062; and 5,735,811). Ultrasonic devices used for vascular treatments typically comprise an extracorporeal transducer coupled to a solid metal wire which is then threaded through the blood vessel and placed in contact with the occlusion (see, U.S. Pat. No. 5,269,297). In some cases, the transducer is delivered to the site of the clot, the transducer comprising a bendable plate (see, U.S. Pat. No. 5,931,805).

The ultrasonic energy produced by an ultrasonic probe is in the form of very intense, high frequency sound vibrations which result in powerful chemical and physical reactions in the water molecules within a body tissue or surrounding fluids in proximity to the probe. These reactions ultimately result in a process called "cavitation," which can be thought of as a form of cold (i.e., non-thermal) boiling of the water in the body tissue, such that microscopic bubbles are rapidly created and destroyed in the water creating cavities in their wake. As surrounding water molecules rush in to fill the cavity created by collapsed bubbles, they collide with each other with great force. This process is called cavitation and results in shock waves running outward from the collapsed bubbles which can wear away or destroy material such as surrounding tissue in the vicinity of the probe.

Some ultrasonic probes include a mechanism for irrigating an area where the ultrasonic treatment is being performed (e.g., a body cavity or lumen) to wash tissue debris from the area. Mechanisms used for irrigation or aspiration described in the art are generally structured such that they increase the overall cross-sectional profile of the probe, by including inner and outer concentric lumens within the probe to provide irrigation and aspiration channels. In addition to making the probe more invasive, prior art probes also maintain a strict orientation of the aspiration and the irrigation mechanism, such that the inner and outer lumens for irrigation and aspiration remain in a fixed position relative to one another, which is generally closely adjacent the area of treatment. Thus, the irrigation lumen does not extend beyond the suction lumen (i.e., there is no movement of the lumens relative to one another) and any aspiration is limited to picking up fluid and/or tissue remnants within the defined distance between the two lumens.

Another drawback of existing ultrasonic medical probes is that they typically remove tissue slowly in comparison to instruments which excise tissue by mechanical cutting. Part of the reason for this is that most existing ultrasonic devices rely on a longitudinal vibration of the tip of the probe for their tissue-disrupting effects. Because the tip of the probe is vibrated in a direction in line with the longitudinal axis of the probe, a tissue-destroying effect is only generated at the tip of the probe. One solution that has been proposed is to vibrate the tip of the probe in a transverse direction-i.e. perpendicular to the longitudinal axis of the probe, in addition to vibrating the tip in the longitudinal direction. For example, U.S. Pat. No. 4,961,424 to Kubota, et al. discloses an ultrasonic treatment device which produces both a longitudinal and transverse motion at the tip of the probe. The Kubota, et al. device, however, still relies solely on the tip of the probe to act as a working surface. Thus, while destruction of tissue in proximity to the tip of the probe is more efficient, tissue destruction is still predominantly limited to the area in the immediate vicinity at the tip of the probe. U.S. Pat. No. 4,504,264 to Kelman discloses an ultrasonic treatment device which improves the speed of ultrasonic tissue removal by oscillating the tip of the probe in addition to relying on longitudinal vibrations. Although tissue destruction at the tip of the device is more efficient, the tissue destroying effect of the probe is still limited to the tip of the probe.

There is a need in the art for improved devices, systems, and methods, for treating vascular diseases, particularly stenotic diseases which occlude the coronary and other arteries. In particular, there is a need for methods and devices for enhancing the performance of angioplasty procedures, where the ability to introduce an angioplasty catheter through a wholly or partly obstructed blood vessel lumen can be improved. There is also a need for mechanisms and methods that decrease the likelihood of subsequent clot formation and restenosis.

SUMMARY OF THE INVENTION

The invention is directed to a method and an apparatus for removing occlusions in a blood vessel. The invention has particular application in removal of occlusions in saphenous vein grafts used in coronary bypass procedures, restoring these grafts to patency without damaging anastomosing blood vessels. The method according to the invention comprises inserting a probe member comprising a longitudinal axis into a vessel, positioning the member in proximity to the occlusion, and providing ultrasonic energy to the member. The device is designed to have a small cross-sectional profile, which also allows the probe to flex along its length, thereby allowing it to be used in a minimally-invasive manner. The probe, because it vibrates transversely, generates a plurality of cavitation anti-nodes along the longitudinal axis of the member, thereby efficiently destroying the occlusion. A significant feature of the invention is the retrograde movement of debris, e.g., away from the tip of the probe, resulting from the transversely generated energy. Probes of the present invention are described in the Applicant's co-pending provisional applications U.S. Ser. Nos. 60/178,901 and 60/225,060 which further describe the design parameters from an ultrasonic probe operating in a transverse mode and the use of such a probe to remodel tissues. The entirety of these applications are herein incorporated by reference.

In one aspect, the invention relates to one or more sheaths which can be adapted to the probe tip, thereby providing a means of containing, focusing, and transmitting energy generated along the length of the probe to one or more defined locations. Sheaths for use with an ultrasonic medical device are described in the Applicant's co-pending utility application U.S. Ser. No. 09/618,352, now U.S. Pat. No. 6,551,337, the entirety of which is hereby incorporated by reference. The sheaths of the present invention also provide the user with a means of protecting regions of tissue from physical contact with the probe tip. In one embodiment of the invention the sheaths also comprise a means for aspiration and irrigation of the region of probe activity. In another embodiment of the invention, a plurality of sheaths are used in combination to provide another level of precision control over the direction of cavitation energy to a tissue in the vicinity of the probe. In one embodiment of the invention, the sheath encloses a means of introducing fluid into the site of the procedure, and a means of aspirating fluid and tissue debris from the site of the procedure. In a further embodiment, the probe tip can be moved within the sheath. In yet another embodiment, the irrigation and aspiration means, and the probe tip, can all be manipulated and repositioned relative to one another within the sheath. In another embodiment, the sheath is shaped in such a way that it may capture or grasp sections of tissue which can be ablated with the probe. In yet another embodiment, the sheath provides a guide for the probe tip, protecting tissues from accidental puncture by the sharp, narrow diameter tip, or from destruction by energy emitted radially from the probe during introduction of the probe to the site. The sheath may be applied to the probe tip prior to insertion of the probe into the patient, or the sheath can be inserted into the patient prior to the insertion of the probe. The sheath of the present invention can be used to fix the location of one or more shapes relative to the nodes or anti-nodes of a probe acting in transverse action. The location of the reflective shapes can amplify the acoustical wave thereby magnifying the energy. This allows for the use of very small diameter probes which themselves would not have the requisite structural integrity to apply and translate acoustical energy into sufficient mechanical energy to enable ablation of tissues. The reflective shapes can also focus or redirect the energy, effectively converting a transverse probe emitting cavitation energy along its length, to a directed, side fire ultrasonic device.

In another embodiment, the probe, which may or may not contain a probe sheath, is used in conjunction with an expandable balloon dilatation catheter, providing a means of resolving the occlusion without imparting stress, or inflicting stress injury to a vessel. The balloon catheter acts as a carrier means for guiding the probe wire to the desired site, and acts as a means to position the wire within the lumen of the vessel. With the balloon inserted within the confines of an occlusion, inflation of the balloon provides a means of continuous contact with the potentially irregularly shaped vessel lumen. Introduction of ultrasonic energy into the balloon by the transversely vibrating probe wire thereby results in uniform communication of energy to the regions of the occluded vessel in contact with the balloon. Since the balloon is inflated to much lower pressures than in traditional balloon angioplasty procedure, neither the occlusion or the vessel is compressed, thereby eliminating the problems of stress injury to the vessel. Likewise, as the ultrasound energy fragments the occlusion, the vessel is cleared of the problematic material, rather than simply compressing it into the vessel.

In one embodiment of the invention, a light transmitting element in inserted into the blood vessel along with, or after, the probe (with or without probe sheath) and balloon catheter. The light transmitting element is transmits optical data about the occlusion. In another embodiment of the invention, the probe/sheath and balloon catheter is used with such medical devices, such as a stent, stent graft, trocar, or other such intravascular devices. The invention is particularly useful in clearing occlusions within stents or other such devices where compression is undesirable or not warranted.

In another aspect of the invention, the probe, with or without a probe sheath, and with or without the balloon catheter, may be provided in a sharps container, in the form of a kit. A sharps container of the present invention is the subject of the Applicant's co-pending utility application U.S. Ser. No. 09/775,908, now U.S. Pat. No. 6,527,115, the entirety of which is hereby incorporated by reference. In yet another embodiment, the kit provides instructions, for example, instructions for assembling and tuning the probe, and the appropriate frequency range for the medical procedure. The kit may further comprise packaging whereby the probe, sheath, and balloon catheter are pre-sterilized, and sealed against environmental contaminants. In another embodiment, the container complies with regulations governing the storage, handling, and disposal of sharp medical devices, and used medical devices such as a sheath or balloon catheter.

DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

In one embodiment, as shown in FIG. 1, the transverse mode ultrasonic medical device 1 comprises an elongated probe 6 which is coupled to a device providing a source or generation means for the production of ultrasonic energy (shown in phantom in the Figure as 66). The probe 6 transmits ultrasonic energy received from the generator along its length. The probe is capable of engaging the ultrasonic generator at one terminus with sufficient restraint to form an acoustical mass, that can propagate the ultrasonic energy provided by the generator. The other terminus of the probe comprises a tip 22, which has a small diameter enabling the tip to flex along its longitude. In one embodiment of the invention, the probe diameter decreases at defined intervals 14, 18, 20, and 22. Energy from the generator is transmitted along the length of the probe, causing the probe to vibrate. In this embodiment, one of the probe intervals 18 has at least one groove 45.

FIG. 2 shows an embodiment of the invention wherein the probe 6 is substantially contained within a cylindrical sheath 121 capable of modulating the energy omitted by an active probe, and shielding tissues from puncture from a sharp probe tip. The sheath 121 shown in this illustration has been modified such that one of the terminal ends of the sheath is substantially open, defining a fenestration or aperture 111, which exposes the probe tip 22 and 23. The terminus of the sheath 129 is shaped to provide a means for manipulating tissue to bring it into proximity with the probe 22 and 23. Also shown in this embodiment is a second cylindrical sheath 108 which surrounds a portion of the first sheath 121, and can be manipulated longitudinally along the first sheath to provide a means for modulating the exposure of the probe tip 22 and 23, and thereby modulating the cavitation energy emitted by the probe to which the tissues will be exposed. The container of the present invention is capable of receiving and containing the probe or probe and sheath assembly.

FIG. 3a shows a transverse mode probe according to one embodiment of the invention comprising the semi-cylindrical sheath 107 and a second sheath 108. In this embodiment, the second sheath is cylindrical, and is capable of containing the first sheath 107, as well as the probe 6.

FIG. 3b shows another embodiment of the invention wherein the sheath 121 comprises a cylindrical structure of a sufficient diameter to contain the probe 6, visible for the purpose of illustration. The sheath 121 comprises at least one fenestration 111, which allows the cavitation energy emitted from the probe tip to be communicated to an area outside the sheath, otherwise the energy is contained by the sheath.

FIG. 3c shows an embodiment of the present invention wherein the hollow cylindrical sheath 121 has a plurality of arcutate fenestrations 111.

FIG. 3d shows an embodiment of the present invention wherein the probe 6 is contained within a sheath 121 which comprises a plurality of arcutate fenestrations 111, and at least one acoustic reflective element 122, which is adapted to the interior surface of the sheath.

FIG. 3e shows an embodiment of the present invention comprising a sheath 121 further comprising two semi-cylindrical halves 109, each half connected to the other by one or more connecting means 113. The probe 6 is capable of being substantially contained within the sheath. The cavitation energy generated by the probe tip 22 is contained by the semi-cylindrical halves 109, wherein they occlude the probe tip.

FIG 3f shows an embodiment of the present invention wherein the sheath further comprises at least two cylinders 104, each cylinder connected to the other by at least one connecting means 113. The probe 6 is capable of being substantially contained within the sheath. The cavitation energy generated by the probe tip 22 is contained by the cylinders 104, where they occlude the probe tip.

FIG. 6a shows an embodiment of the invention wherein the probe tip 22 and 23, is substantially contained within a sheath. The sheath comprises a fenestration 111 allowing communication of the cavitation energy emitted by the probe to the outside of the sheath. The interior of the sheath further comprises reflective elements 118, shown as a plurality of planar surfaces that extend from the interior wall of the sheath into the lumen, thereby providing a means for focusing and redirecting cavitation energy omitted by the probe tip. In this embodiment, the terminus of the sheath 129 is shaped to provide a tissue manipulation means also illustrated in FIG. 5.

FIG. 7 shows the ultrasonic medical device comprising an ultrasonic probe for removal of an occlusion "O" from a blood vessel "BV".

FIG. 8 shows the ultrasonic medical device comprising an ultrasonic probe and a sheath assembly for selectively ablating an occlusion "O" from a blood vessel "BV".

FIG. 9 shows the ultrasonic medical device used in conjunction with a balloon catheter for removal of an occlusion "O" from a blood vessel "BV".

FIG. 10 shows the ultrasonic medical device used in conjunction with a series of sheaths and a balloon catheter 91.

DETAILED DESCRIPTION

Figure 3A:
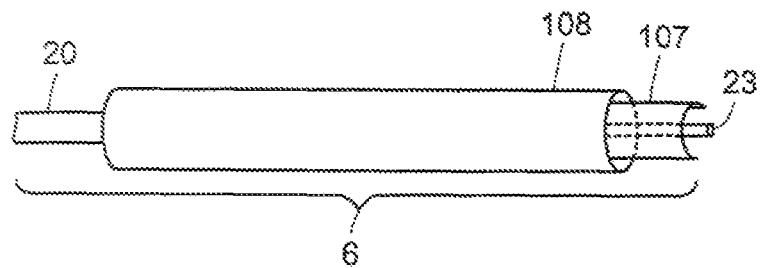
FIGS. 3a-f show dampening sheaths for an ultrasonic probe according to embodiments of the invention.
Figure 3B:
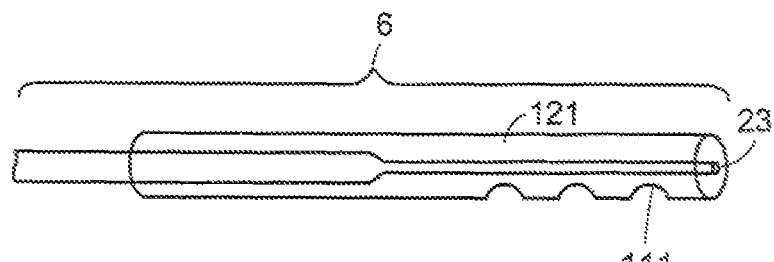
Figure 3C:
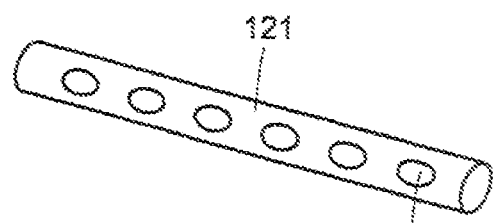
Figure 3D:
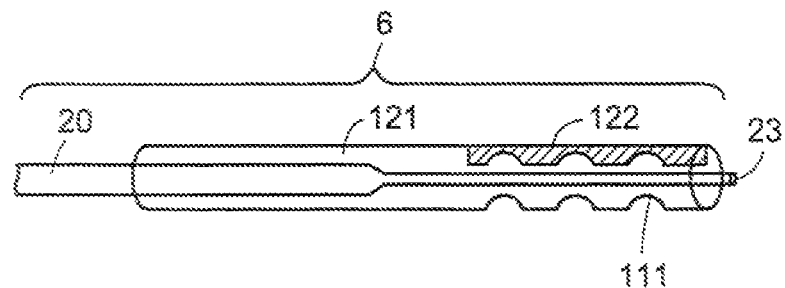
Figure 3E:
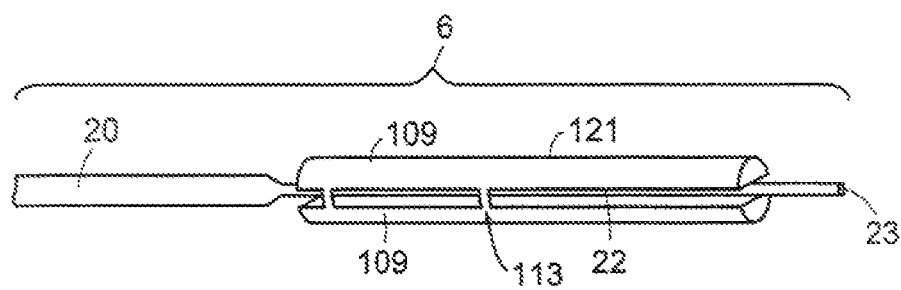
Figure 3F:
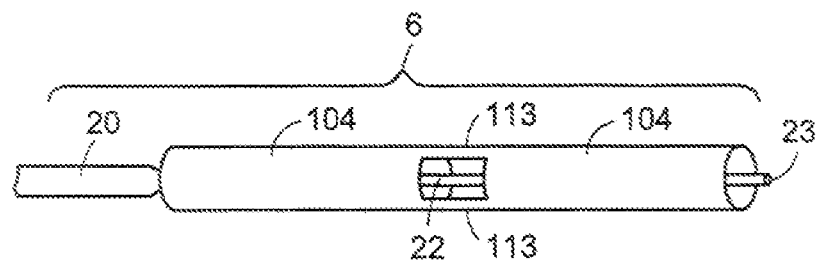
Figure 4:
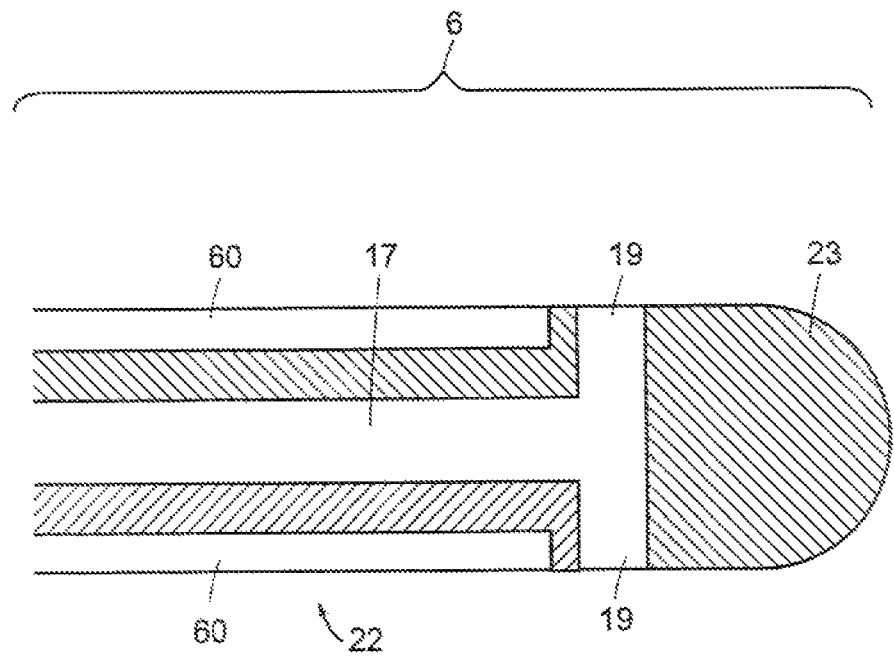
FIG. 4 shows a longitudinal cross-section of a portion of an ultrasonic probe tip 22 and 23 according to one embodiment of the invention, comprising a central irrigation passage 17 and lateral irrigation lumens 19, as well as external aspiration channels 60.

The following terms and definitions are used herein:

"Anti-node" as used herein refers to a region of maximum energy emitted by an ultrasonic probe on or proximal to a position along the probe.

"Cavitation" as used herein refers to shock waves produced by ultrasonic vibration, wherein the vibration creates a plurality of microscopic bubbles which rapidly collapse, resulting in molecular collision by water molecules which collide with force thereby producing the shock waves.

"Fenestration" as used herein refers to an aperture, window, opening, hole, or space.

"Node" as used herein refers to a region of minimum energy emitted by an ultrasonic probe on or proximal to a position along the probe.

"Probe" as used herein refers to a device capable of being adapted to an ultrasonic generator means, which is capable of propagating the energy emitted by the ultrasonic generator means along its length, and is capable of acoustic impedance transformation of ultrasound energy to mechanical energy.

"Sharps" as used herein refers to an elongated medical instrument with a small diameter, for example, less than 2 mm. A "Sharps Container" as used herein is a container capable of retaining a sharp medical device or the sharp portion thereof, such that a handler is not exposed to the sharp portion of the device.

"Sheath" as used herein refers to a device for covering, encasing, or shielding in whole or in part, a probe or portion thereof connected to an ultrasonic generation means.

"Tissue" as used herein refers to an aggregation of cells that is substantially similar in terms of morphology and functionality.

"Transverse" as used herein refers to vibration of a probe at right angles to the axis of a probe. A "transverse wave" as used herein is a wave propagated along an ultrasonic probe in which the direction of the disturbance at each point of the medium is perpendicular to the wave vector.

"Tuning" as used herein refers to a process of adjusting the frequency of the ultrasonic generator means to select a frequency that establishes a standing wave along the length of the probe.

"Ultrasonic" as used herein refers to a frequency range of the electromagnetic spectrum above the range of human hearing, i.e., greater than about 20,000 Hertz up to about 80,000 Hertz.

The present invention provides an ultrasonic medical device operating in a transverse mode for removing a vascular occlusion. Because the device is minimally invasive and articulable, it can be inserted into narrow, tortuous blood vessels without risking damage to those vessels. Transverse vibration of the probe in such a device generates multiple anti-nodes of cavitation energy along the longitudinal axis of the probe, emanating radially from these anti-nodes. The occlusion is fragmented to debris approximately of sub-micron sizes, and the transverse vibration generates a retrograde flow of debris that carries the debris away from the probe tip.

The mode of vibration of the ultrasound probe according to the invention differs from the axial mode of vibration which is conventional in the prior art. Rather than vibrating exclusively in the axial direction, the probe vibrates in a direction transverse to the axial direction. As a consequences of the transverse vibration of the probe, the tissue-destroying effects of the device are not limited to those regions of a tissue coming into contact with the tip of the probe. Rather, as the probe is positioned in proximity to an occlusion or other blockage of a blood vessel, the tissue is removed in all areas adjacent to the multiplicity of energetic anti-nodes being produced along the entire length of the probe typically in a region having a radius of up to about 2 mm around the probe. In this way, actual treatment time using the transverse mode ultrasonic medical device according to the invention is greatly reduced as compared to methods using prior art probes.

The number of anti-nodes occurring along the axial length of the probe is modulated by changing the frequency of energy supplied by the ultrasonic generator. The exact frequency, however, is not critical and a ultrasonic generator run at, for example, 20 kHz is generally sufficient to create an effective number of tissue destroying anti-nodes along the axial length of the probe. In addition, as will be appreciated by those skilled in the art, it is possible to adjust the dimensions of the probe, including diameter, length, and distance to the ultrasonic energy generator, in order to affect the number and spacing of anti-nodes along the probe. The present invention allows the use of ultrasonic energy to be applied to tissue selectively, because the probe conducts energy across a frequency range of from about 20 kHz through about 80 kHz. The amount of ultrasonic energy to be applied to a particular treatment site is a function of the amplitude and frequency of vibration of the probe. In general, the amplitude or throw rate of the energy is in the range of 150 microns to 250 microns, and the frequency in the range of 20-80 kHz. In the currently preferred embodiment, the frequency of ultrasonic energy is from 20,000 Hertz to 35,000 Hertz. Frequencies in this range are specifically destructive of hydrated (water-laden) tissues and vascular occlusive material, while substantially ineffective toward high-collagen connective tissue, or other fibrous tissues such as, for example, vascular tissues, or skin, or muscle tissues,.

The amount of cavitation energy to be applied to a particular site requiring treatment is a function of the amplitude and frequency of vibration of the probe, as well as the longitudinal length of the probe tip, the proximity of the tip to a tissue, and the degree to which the probe tip is exposed to the tissues. Control over this last variable can be effectuated through the sheaths of the present invention.

Sheath materials useful for the present invention include may material with acoustical or vibrational dampening properties capable of absorbing, containing, or dissipating the cavitation energy emitted by the probe tip. Such materials must be capable of being sterilized by, for example, gamma irradiation or ethylene oxide gas (ETO), without losing their structural integrity. Such materials include but are not limited to, plastics such as polytetrafluoroethylene (PTFE), polyethylene, polypropylene, silicon, ultem, or other such plastics that can be used for medical procedures. Ceramic materials can also be used, and have the added benefit that they may be sterilized by autoclaving. Combinations of the aforementioned materials can be used depending on the procedure, for example as in the sheath of FIG. 5, a ceramic sheath 121 can be used in combination with a moveable PTFE outer sheath 108. Alternatively a single sheath may employ two or more materials to give the desired combination of strength and flexibility, for example, the sheath may comprise a rigid ceramic section distal to the probe tip 23 and a more flexible plastic section proximal to the tip, capable of flexing with the probe 22. In the currently preferred embodiment of the invention, PTFE is used to fabricate a strong, flexible, disposable sheath that is easily sterilized by irradiation or ETO gas.

The length and diameter of the sheath used in a particular operation will depend on the selection of the probe, the degree to which the probe length will be inserted into the subject, and the degree of shielding that is required. For example, in an application whereby vascular occlusive material is removed with the ultrasonic probe of the present invention, from a vessel deep inside the body of a patient, the sheath must be of a sufficient length to protect the vascular tissue from the surgical insertion point to the site of the operation, of a sufficient outside diameter to facilitate insertion of the sheath into the vessel, and a sufficient inside diameter capable of accepting the probe. By contrast, for clearing occlusions from, for example, a hemodialysis graft, the probe useful for such a procedure would be significantly shorter and as such, so would the sheath. The exact length and diameter of the sheath will be determined by the requirements of the medical procedure. Similarly, the position and size of the sheath aperture 111, or number and positions of the fenestrations 111, or the addition of a bevel on the sheath terminus 129, will likewise be determined by the type of procedure, and the requirements of the particular patient.

Figure 6B:
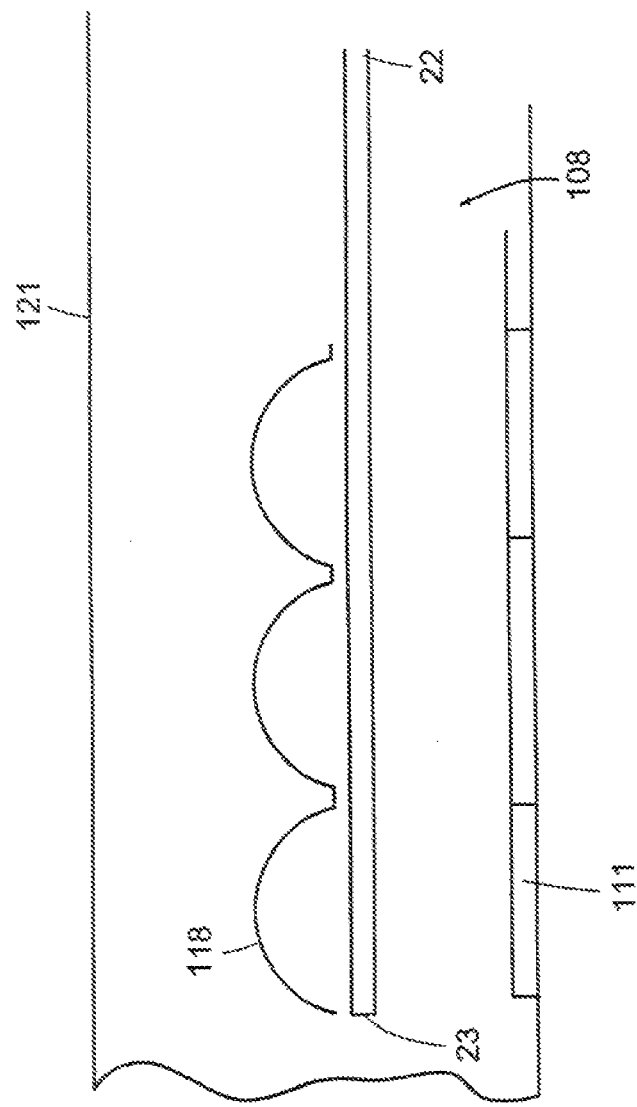
FIG. 6b shows a similar embodiment, wherein the reflective elements 118 are arcutate, and the sheath further comprises a plurality of fenestrations 111.
Figure 7A:
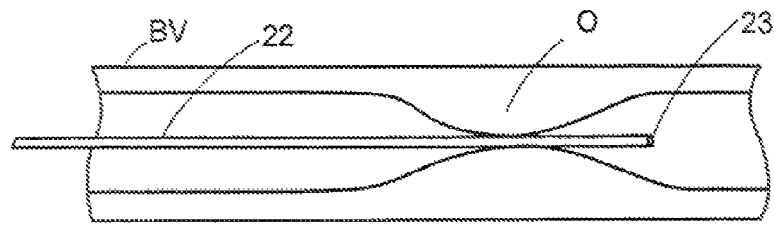
FIG. 7a shows a portion of the probe 22 guided to the site of, and through the occlusion, using ultrasonic energy to fragment occlusion materials and clear a path through the occlusion.
Figure 7B:
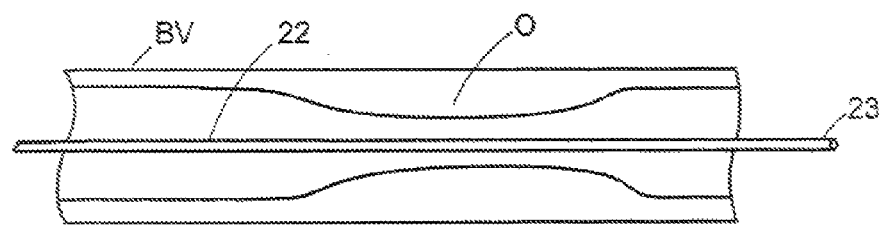
FIG. 7b shows the occlusion within the blood vessel partially removed by action of the probe.
Figure 7C:
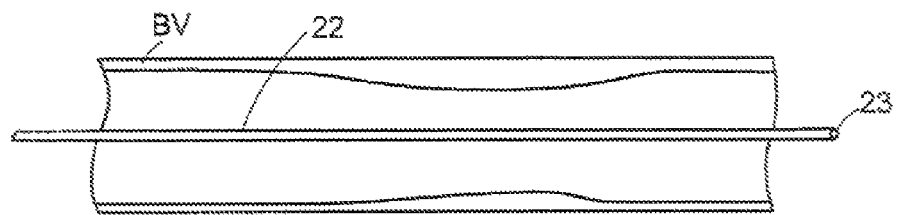
FIG. 7c shows complete removal of the occlusion as occlusion materials are degraded by the energy transmitted by the probe 22 of the ultrasonic medical device.

A particular advantage of the ultrasonic probe operating in transverse mode is that the efficient cavitation energy produced by the probe disintegrates target tissue to small particles of approximately sub-micron diameter. Because of the operation of the probe, tissue debris created at the probe tip 23, is propelled in a retrograde direction from the probe tip. Accordingly, another embodiment of the invention, provides at least one aspiration channel which can be adapted to a vacuum or suction device, to remove the tissue debris created by the action of the probe. The aspiration channel can be manufactured out of the same material as the sheath provided it is of a sufficient rigidity to maintain its structural integrity under the negative pressure produced by the aspiration means. Such an aspiration channel could be provided inside the lumen of the sheath, or along the exterior surface of the sheath, or the sheath itself may provide the aspiration channel. One embodiment of this is shown in FIGS. 6 and 7, whereby the probe 22 comprises at least one aspiration channel 60, and aspiration of tissue debris is effectuated along the probe length between the interior surface of the sheath and the exterior surface of the probe, as directed by the aspiration channels.

In another embodiment, the present invention comprises an irrigation channel. The sheath is adapted to an irrigation means, and the sheath directs fluid to the location of the probe 22. The irrigation channel can be manufactured out of the same material as the sheath provided it is of a sufficient rigidity to maintain its structural integrity under the positive pressure produced by the flow of fluid produced by the irrigation means. Such an irrigation channel could be provided inside the lumen of the sheath, or along the exterior surface of the sheath, or the sheath itself may provide the aspiration channel. Using the sheath itself to provide the irrigation, there is an added benefit that the probe 22 is cooled by the fluid.

In yet another embodiment, the sheath of the present invention further comprises both an irrigation and an aspiration channel. As in the above embodiment, the channels may be located within the sheath lumen, or exterior to the sheath, or a combination of the two. Likewise, the sheath lumen itself may provide either an irrigation or aspiration channel, with the corresponding irrigation or aspiration channel either contained within or external to the sheath. In another aspect of the invention, the sheath comprises a means for directing, controlling, regulating, and focusing the cavitation energy emitted by the probe, an aspiration means, an irrigation means, or any combination of the above.

Another embodiment of the invention comprise a means of viewing the site of probe action. This may include an illumination means and a viewing means. In one embodiment, the sheath of the present invention comprises a means for containing or introducing (if external to the sheath) an endoscope, or similar optical imaging means. In another embodiment of the invention, the ultrasound medical device is used in conjunction with an imaging system, for example, the non-ferrous probes are compatible with MRI, or ultrasound imaging—in particular color ultrasound. In this embodiment, the action of the probe echogenically produces a pronounced and bright image on the display. The sheath in this embodiment shields the probe, thereby reducing the intensity of the probe image and enhancing the resolution of the surrounding tissues. In another embodiment of the invention (not shown), the probe is used with an optical system. In one embodiment, the probe is inserted into a body cavity or lumen along with a light transmitting element for transmitting light from a light source and for receiving light and transmitting received light to a detector. Light from a light source (e.g., a laser) is transmitted through the light transmitting element, illuminating the area surrounding the probe 6, and light transmitted back through the light transmitting element (e.g., from tissue in the vicinity of the probe) is detected by the detector. In one embodiment of the invention, the light transmitting element is an optical fiber, while in another embodiment, the light transmitting element is a plurality of optical fibers. The light transmitting element can be a part of the probe or can be inserted into a body cavity independently of the probe. In one embodiment of the invention, a sleeve is attached to the probe and the light transmitting element is held within the sleeve. In one embodiment, the detector is a human being (e.g., a physician or lab technician) and light is monitored using a viewing element, such as an eyepiece (e.g., as in a microscope coupled to the light transmitting element). It is preferred that the viewing element is not connected to a part of the ultrasonic medical device which is subject to vibration, to reduce manipulation of the viewing system to a minimum. In another embodiment of the invention, the detector is in communication with a processor and converts optical signals from the light transmitting element to data relating to the tissue in the vicinity of the probe.

Figure 8A:
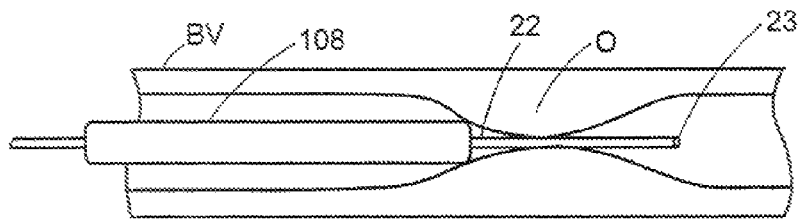
FIG. 8a shows a sheath assembly consisting of a sheath 108 adapted to a portion of the probe 22. The probe is positioned proximally to the site of, and through the occlusion, using ultrasonic energy to fragment occlusion materials and clear a path through the occlusion, while the sheath protects non-occluded areas of the blood vessel by partially shielding the probe.
Figure 8B:
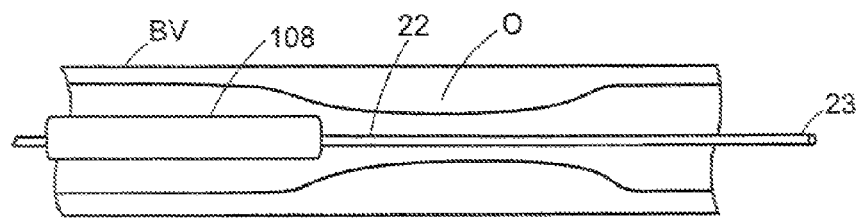
FIG. 8b shows the occlusion within the blood vessel partially removed by action of the probe, while the sheath is retracted to maintain exposure of the probe at occlusion site as it is moved through the site.
Figure 8C:
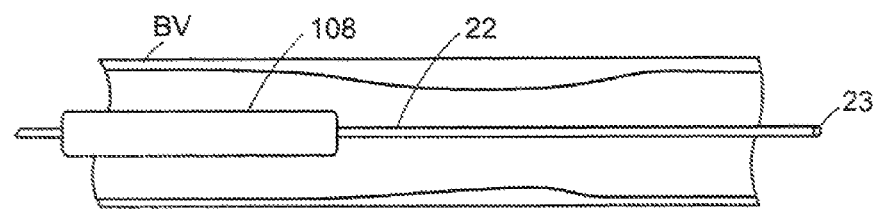
FIG. 8c shows complete removal of the occlusion, as occlusion materials are degraded by the energy transmitted by the probe 22 of the device, while non-occluded areas of the blood vessel remain protected from the action of the probe.
Figure 9A:
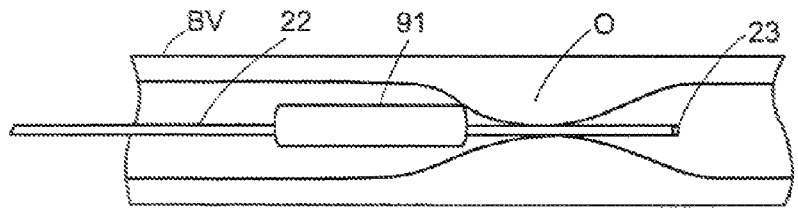
FIG. 9a shows a deflated balloon catheter 91 adapted to a portion of a probe 22. The probe guides the catheter to the site of, and through the occlusion, using ultrasonic energy to clear path through the occlusion if necessary.
Figure 9B:
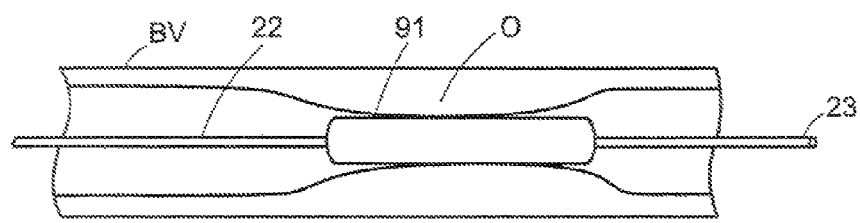
FIG. 9b shows the deflated balloon catheter 91 positioned within the vessel lumen at the site of the occlusion.
Figure 9C:
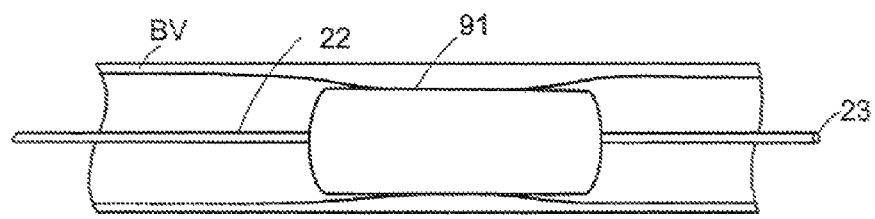
FIG. 9c shows an activated ultrasonic medical device wherein the expanded balloon catheter engages the occlusion, maintaining contact with the occlusion as it is degraded by the energy transmitted through the balloon.

In one embodiment, as shown in FIG. 8, the sheath comprises a surface that is capable of manipulating tissues near the site of the probe. In this aspect, the terminus of the sheath may be closed, such that the sheath insulates tissues from the destructive energy emitted by the probe and can be used to push tissues away from the aperture 111, thereby allowing proximal tissues to be exposed to the probe 22 and 23. Alternatively, the sheath comprises a beveled or arcutate surface at the sheath terminus 129, capable of providing a means for hooking, grasping, or otherwise holding a tissue in proximity to the probe 22 and 23. In another embodiment, the sheath provides a means for introducing a surgical device, for example, flexible biopsy forceps, capable of manipulating tissues into a tissue space, such that the surgical device can hold the tissue in proximity with the probe.

Figure 5:
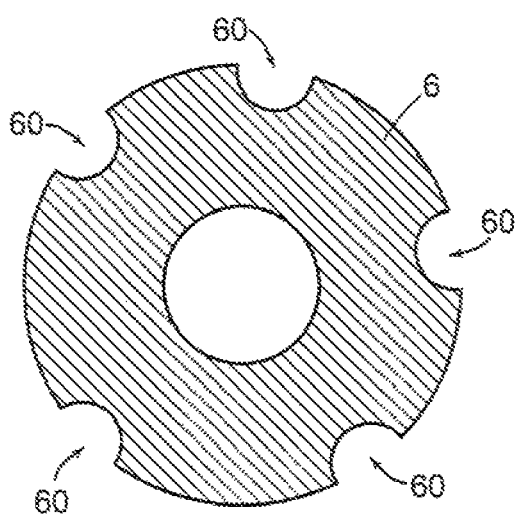
FIG. 5 shows a transverse cross-section of a portion of the ultrasonic probe shown in FIG. 4. In this embodiment, the probe 6 comprises a plurality of arcutate channels 60 that extend over the longitudinal length of the probe tip, providing a space for irrigation and or aspiration of tissue debris and fluid.
Figure 10A:
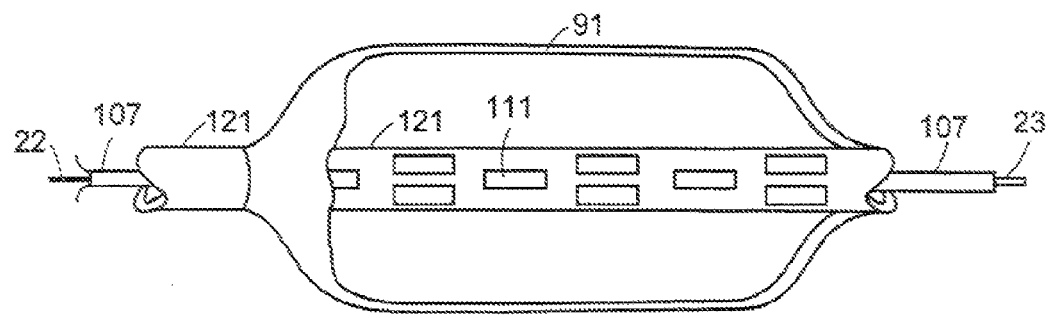
In FIG. 10a, the invention of the present embodiment comprises a probe 22 with a terminal end 23, substantially contained within a first sheath 107 of which the end distal to the probe tip 23, is shown cut away from illustrative purposes. The balloon catheter is adapted to an inflation means (not shown), which may also comprise a means for monitoring and compensating for pressure fluctuation in the interior of the balloon. The probe and first sheath is substantially contained within a second sheath 121, further comprising a series of fenestrations 111 along its longitude. The balloon catheter 91, shown substantially deflated, surrounds the second sheath along part of its length. In this embodiment, the probe tip 23 is exposed to the vessel lumen and can provide a means for clearing a path through an occlusion for the introduction of a balloon catheter.
Figure 10B:
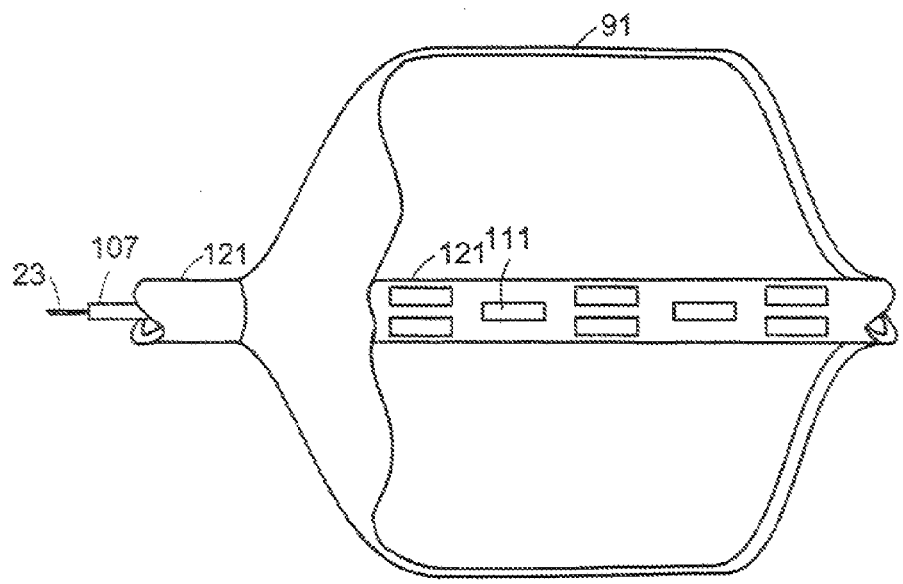
In FIG. 10b, the probe 22 and 23 is withdrawn such that the tip 23, is contained within the sheath 121. The first sheath 107 is retracted, by for example, articulation wires, thereby exposing the probe 22 to the lumen of the second sheath 121. Activation of the probe results in the transverse generation of cavitation energy along the probe at multiple anti-nodes. The energy is communicated from the probe to the lumen of the balloon catheter through the fenestrations 111 in the second sheath 121. The energy can penetrate the walls of the balloon for direct communication to the occlusion.

In one aspect of the invention, as shown in FIG. 5, the sheath comprises an inner sheath 121 and an outer sheath 108. The outer sheath may be connected to an retraction trigger (not shown), by one or more articulation means, such as wires, which is capable of moving the outer sheath with respect to the inner sheath. Each wire comprises a first end and second end. The first end is affixed to the outer sheath 108, while the second end is affixed to a retraction trigger. When the outer sheath 108 is slid back away from the terminus of the inner sheath 121 the tissues are exposed to cavitation energy emitted by the probe. Another aspect of this is referred to in FIG. 10, where the firt sheath 107, is adapted to articulation wires (not shown in the illustration). In this embodiment, moving the sheath exposes the probe to the lumen of a second sheath 121, comprising fenestrations which allow communication of the energy emitted from the probe to the lumen of a balloon catheter 91. In this aspect, a probe can be operational without inflating the balloon catheter until movement of the first sheath exposes the probe, thereby allowing the probe to penetrate occlusions that would otherwise prevent placement of the balloon catheter without first clearing a site for placement within the occlusion, and thereby reducing the number of steps in a surgical procedure.

In another embodiment, the probe and sheath are flexible. Articulation wires (not shown) comprising a first end and second end, are connected to the sheath and to an articulation handle. When the articulation handle is manipulated, for example, pulled axially inward, the flexible sheath will bend or articulate in a bending or articulation direction A, thereby causing the ultrasonic probe to bend or articulate in articulation direction A. In this way, the ultrasonic probe can be used to reach locations which are not axially aligned with the lumen or vessel through which the sheath and probe are inserted. One aspect of the invention uses such an articulable sheath to direct placement of a probe and a balloon catheter to a surgical site.

In yet another embodiment, the sheaths of the present invention may be provided along with an ultrasonic probe in the form of a kit. In this aspect, the probe for a particular surgical procedure is provided along with the correct sheath, as well as instructions for assembling and tuning the probe, and the appropriate frequency range for the procedure. The probe and sheath may be packaged preassembled, such that the probe is already contained within the sheath and the respective position of the probe within the sheath is optimized such that any reflective elements in the sheath would be correctly aligned with the prospective position of the antinodes for a given frequency, the kit further comprising instructions for the appropriate frequency. The kit may further comprise packaging whereby the probe and sheath are pre-sterilized, and sealed against contaminants. In another embodiment, the probe and sheath is provided in a container that complies with regulations governing the storage, handling, and disposal of sharp medical devices. Such a container is capable of receiving and securing the probe and sheath before and after use. In one aspect, the sharps container provides a means of affixing the probe and sheath assembly to an ultrasonic medical device without direct manipulation of the probe and sheath assembly, and a means for removing the assembly from the ultrasonic medical device after use. In one aspect, the kit comprises a probe and sheath assembly contained within a sterile sharps container that further comprises a single use locking means, whereby the probe and sheath assembly is affixed to the ultrasonic medical device solely through the sharps container, are removed from the device solely through the container, and once removed can not be re-extracted from the sharps container.

EXAMPLES

Example 1

Removing Occlusions Using an Ultrasonic Medical Device and a Balloon Catheter

In one embodiment of the invention, the transverse mode ultrasonic medical device, is used in a procedure to remove an occlusion from a small diameter vessel (e.g., a native vessel, or a grafted vessel). In one embodiment, device is used in a method to reduce or eliminate an occlusion of a saphenous vein graft (e.g., such as used in a coronary bypass procedure).

A transverse mode ultrasonic probe is selected by the surgeon who will perform the procedure. The probe of the present invention further comprises a plurality of sheaths adapted to the probe, and a balloon catheter operably attached to one of the sheaths, all incorporated within a sharps container, and the container further sealed inside a sterile package, for example, a plastic bag. The user removes the container from the package and attaches the probe to the ultrasonic medical device by applying the threaded end of the probe to the transducer portion of an ultrasonic medical device. The probe, sheaths, and balloon catheter are securely held within the container, and the user rotates the container to affix the probe, sheaths, and catheter to the ultrasonic medical device. The user engages a lever which articulates the side A first locking assembly, thereby disengaging the probe from the first locking assembly. The probe, sheaths, and catheter can now be withdrawn from the container. The first locking assembly, once articulated, is engaged and held stationary by a second locking means, thereby preventing further use of the first locking assembly on this side A of the container with a probe. Articulation wires attached to one of the sheaths, are connected to a trigger assembly so the first sheath can be moved relative to the second sheath and the probe. One terminus of the balloon catheter is connected to an inflation means that may further comprise a means of monitoring and adjusting for pressure changes in the balloon lumen.

A small incision is made into the chest of a patient, and the vein graft is visualized using routine imaging technology. The probe, sheaths, and balloon catheter assembly is introduced into a vessel near the site of the occlusion, by way of, for example, a trocar or other vascular introducer. The probe assembly is guided to the site of the occlusion. The probe may be operably emitting energy, but the position of the first sheath relative to the probe and second sheath prevents cavitation energy from the probe from entering the balloon catheter, and the exposed probe terminus allows for introduction of the assembly, specifically the balloon catheter into the interior of the occlusion, as the occlusion is fragmented around the probe. The balloon catheter is inflated to greater than ambient pressure, such as for example, 1.5 atmospheres, so that the balloon is in contact with the occlusion but does not exert a high degree of compressive force on the occlusion or the vessel wall. The transversely vibrating probe is exposed to the lumen of the balloon by articulation of the first sheath. Cavitation energy from the probe is transmitted to the occlusion through the polymer walls of the balloon, thereby fragmenting the occlusion. As the occlusion is destroyed, allowing expansion of the balloon, the pressure drop is sensed and compensated for, by the inflation means, thereby the balloon re-engages the surface of the occlusion. The process continues for an appropriate length of time determined by the surgeon. When the procedure is completed, the balloon catheter is deflated, and the catheter, sheaths, and probe are withdrawn from the patient. The insertion device is removed, and the vascular tear, and surgical incision are sutured.

When the user completes the surgical procedure, and the probe apparatus is no longer required, the user inserts the probe, sheaths, and balloon catheter into side B of the container. The user engages a lever which articulates the side B first locking assembly, which, once articulated, is engaged and held stationary by a second locking means, thereby preventing further articulation of the side B first locking assembly. This first locking assembly engages the probe, thereby securing it. The user removes the probe assembly from the transducer of the medical device by applying counter-rotational torque to the container, thereby unscrewing the probe from the device. The used probe and assembly is permanently engaged by and contained within the container, and can be disposed of in compliance with the provisions governing the disposal of medical waste. Because the probe assembly is contained by the invention, the sharp probe tip does not present a safety hazard, and can be safely handled and disposed of as medical trash.

Example 2

Clearing Occlusions from a Hemodialysis Graft

In another embodiment, the invention can be used to clear occlusions from and restore the patency of a hemodialysis graft. The graft will not require shielding from ultrasonic energy, or the use of a balloon catheter as in example 1. A probe is selected and affixed to the ultrasonic transducer in the manner previously described, through the use of the container. The probe is withdrawn from the container, and inserted into the lumen of the hemodialysis graft. In one embodiment, the probe is directly introduced into the hemodialysis graft. In another embodiment, the probe is inserted using a trocar or other vascular insertion device, such as for example, the insertion device of Applicant's utility application 09/618,352, now U.S. Pat. No. 6,551,337. Application of ultrasonic energy causes the probe to vibrate transversely along its longitude. Occlusive materials, such as for example a thrombus, are fragmented by the action of the probe. When the graft has been returned to patency, the probe is withdrawn. The probe is removed from the device with the sharps container.

Variations, modifications, and other implementations of what is described herein will occur to those of ordinary skill in the art without departing from the spirit and scope of the invention as claimed. Accordingly, the invention is to be defined not by the preceding illustrative description but instead by the spirit and scope of the following claims. The following references provided include additional information, the entirety of which is incorporated herein by reference.

We claim:

1. A medical system for removal of occlusions in blood vessels, the medical system comprising:
    a flexible ultrasonic probe, the flexible ultrasonic probe having a proximal probe end and distal probe end, wherein the flexible ultrasonic probe has a plurality of nodes and a plurality of anti-nodes of transverse motion configured to provide transverse vibration; and
    a flexible sheath substantially surrounding the flexible ultrasonic probe having a proximal sheath end and a closed distal sheath end, the flexible sheath defining at least one fenestration located proximate the closed distal sheath end, the at least one fenestration having a proximal fenestration end and a distal fenestration end, wherein the distal probe end of the flexible ultrasonic probe is distal relative to the distal fenestration end such that the probe is configured to side fire cavitation energy.

2. The medical system of claim 1, wherein the flexible sheath defines a plurality of fenestrations.

3. The medical device of claim 1, wherein the flexible sheath is associated with a balloon catheter.

4. The medical device of claim 1, wherein the flexible ultrasonic probe is sized for placement in the vasculature of a patient.

5. The medical system of claim 1, wherein the flexible ultrasonic probe is configured to generate a plurality of anti-nodes along a longitudinal axis of the flexible ultrasonic probe when the flexible ultrasonic probe is vibrated at a frequency of about 20 kHz to about 80 kHz.

6. The medical system of claim 1, wherein the at least one fenestration is arcuate.

7. The medical system of claim 1, wherein the at least one fenestration is a single fenestration.

8. The medical system of claim 1, wherein the distal probe end is substantially contained within the sheath.

9. A medical system for removal of occlusions in blood vessels, the medical system comprising:
    a flexible ultrasonic probe, the flexible ultrasonic probe having a proximal probe end and a distal probe end, wherein the flexible ultrasonic probe provides transverse vibration; and
    a flexible sheath substantially surrounding the flexible ultrasonic probe, the flexible sheath defining at least one fenestration proximate a distal closed end of the flexible sheath, the at least one fenestration having a proximal end and a distal end, wherein the distal probe end of the flexible ultrasonic probe is positioned distally relative to the distal end of the at least one fenestration.

10. The medical system of claim 9, wherein the transverse vibration is emitted by the flexible ultrasonic probe through the at least one fenestration defined by the sheath when the flexible ultrasonic probe is vibrated.

11. The medical system of claim 9, wherein the medical system comprises a plurality of fenestrations.

12. The medical system of claim 11, wherein each of the plurality of fenestrations are positioned proximate the distal closed end of the flexible sheath.

13. The medical system of claim 9, wherein a portion of the flexible ultrasonic probe is disposed adjacent the at least one fenestration of the sheath.

14. The medical system of claim 9, further comprising a flexible outer sheath that surrounds at least a portion of the flexible sheath, the flexible outer sheath and the flexible sheath being axially moveable relative to one another.

15. The medical system of claim 9, wherein the distal probe end is retained within the sheath when vibrating in a transverse mode.

16. The medical system of claim 9, wherein the flexible ultrasonic probe is configured to generate a plurality of anti-nodes along a longitudinal axis of the ultrasonic probe when the flexible ultrasonic probe is vibrated at a frequency of about 20 kHz to about 80 kHz.

17. A medical system for removal of occlusions in blood vessels, the medical system comprising:
- an ultrasonic probe utilizing transverse vibration, the ultrasonic probe having a plurality of nodes and a plurality of anti-nodes of transverse motion;
- a sheath having a proximal end and a closed distal end, the sheath defining a lumen configured to receive and substantially surround the ultrasonic probe, the sheath having a single fenestration proximate the closed distal end of the sheath, wherein the single fenestration is configured to receive transverse vibration therethrough.

18. The medical system of claim 17, wherein the transverse vibration is emitted by the ultrasonic probe through the single fenestration defined by the sheath when the ultrasonic probe is vibrated within the lumen of the sheath.

19. The medical system of claim 17, wherein a distal end of the ultrasonic probe is housed within the sheath when vibrating in a transverse mode.

20. The medical system of claim 17, wherein the ultrasonic probe is disposed adjacent the single fenestration.

\* \* \* \* \*